(12) United States Patent
Sarnaik et al.

(10) Patent No.: US 11,401,506 B2
(45) Date of Patent: Aug. 2, 2022

(54) ENHANCED EXPANSION OF TUMOR-INFILTRATING LYMPHOCYTES FOR ADOPTIVE CELL THERAPY

(71) Applicants: H. Lee Moffitt Cancer Center and Research Institute, Inc., Tampa, FL (US); Board of Regents, The University of Texas System, Austin, TX (US)

(72) Inventors: Amod A. Sarnaik, Tampa, FL (US); Jeffrey S. Weber, Tampa, FL (US); Shari Pilon-Thomas, Tampa, FL (US); Laszlo G. Radvanyi, Lutz, FL (US); Jessica Ann Chacon, Philadelphia, PA (US); James J. Mule, Odessa, FL (US); MacLean S. Hall, Tampa, FL (US)

(73) Assignees: H. Lee Moffitt Cancer Center and Research Institute, Inc., Tampa, FL (US); Board nf Regents The Inivercityof Texas Cvctom, Austin, TX (US)

( * ) Notice: Subject to any disclaimer, the term of this patent is extended or adjusted under 35 U.S.C. 154(b) by 0 days.

(21) Appl. No.: 16/227,824

(22) Filed: Dec. 20, 2018

(65) Prior Publication Data

US 2020/0032209 A1 Jan. 30, 2020

Related U.S. Application Data

(63) Continuation of application No. 15/303,201, filed as application No. PCT/US2015/025313 on Apr. 10, 2015, now abandoned.

(60) Provisional application No. 61/978,112, filed on Apr. 10, 2014.

(51) Int. Cl.
| | | |
|---|---|---|
| *A61K 35/17* | (2015.01) | |
| *C12N 5/0783* | (2010.01) | |
| *A61K 39/00* | (2006.01) | |

(52) U.S. Cl.
CPC ........... *C12N 5/0638* (2013.01); *A61K 35/17* (2013.01); *A61K 39/0011* (2013.01); *A61K 2039/5158* (2013.01); *C12N 2501/2302* (2013.01); *C12N 2501/25* (2013.01); *C12N 2501/599* (2013.01); *C12N 2501/998* (2013.01)

(58) Field of Classification Search
CPC .......... C12N 5/0638; C12N 2501/2302; C12N 2501/599; A61K 39/0011; A61K 35/17
USPC .................................................. 424/277.1
See application file for complete search history.

(56) References Cited

U.S. PATENT DOCUMENTS

| | | |
|---|---|---|
| 5,126,132 A | 6/1992 | Rosenberg |
| 5,443,983 A | 8/1995 | Ochoa et al. |
| 5,925,565 A | 7/1999 | Berlioz et al. |
| 5,935,819 A | 8/1999 | Eichner et al. |
| 6,352,694 B1 | 3/2002 | June et al. |
| 6,534,055 B1 | 3/2003 | June et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,960,648 B2 | 11/2005 | Bonny |
| 7,144,575 B2 | 12/2006 | June et al. |
| 7,175,843 B2 | 2/2007 | June et al. |
| 7,232,566 B2 | 6/2007 | June et al. |
| 7,479,269 B2 | 1/2009 | June et al. |
| 7,572,631 B2 | 8/2009 | Berenson et al. |
| 7,943,743 B2 | 5/2011 | Korman et al. |
| 7,951,365 B2 | 5/2011 | Winqvist et al. |
| 8,007,785 B2 | 8/2011 | Winqvist et al. |
| 8,008,449 B2 | 8/2011 | Korman et al. |
| 8,034,334 B2 | 10/2011 | Dudley et al. |
| 8,206,702 B2 | 6/2012 | Winqvist et al. |
| 8,211,424 B2 | 7/2012 | Winqvist et al. |
| 8,211,425 B2 | 7/2012 | Winqvist et al. |
| 8,383,099 B2 | 2/2013 | Dudley et al. |
| 8,617,884 B2 | 12/2013 | Berenson et al. |
| 8,809,050 B2 | 8/2014 | Vera et al. |
| 8,956,860 B2 | 2/2015 | Vera et al. |
| 9,074,185 B2 | 7/2015 | Dudley et al. |
| 9,476,028 B2 | 10/2016 | Karlsson-Parra et al. |
| 9,528,088 B2 | 12/2016 | Berenson et al. |

(Continued)

FOREIGN PATENT DOCUMENTS

| | | |
|---|---|---|
| EP | 1539929 B1 | 4/2013 |
| EP | 2925329 A1 | 10/2015 |

(Continued)

OTHER PUBLICATIONS

Menzies et al. (European Journal of Cancer, 2013, 49: 3229-3241).*

(Continued)

*Primary Examiner* — Yan Xiao
(74) *Attorney, Agent, or Firm* — Morgan, Lewis & Bockius LLP

(57) ABSTRACT

Disclosed herein is a method for ex vivo expanding tumor-infiltrating lymphocytes for use in adoptive cell therapy (ACT). The method involves culturing tumor fragments from the subject in a culture medium containing IL-2 and a 41BB agonist in an amount effective to expand tumor-infiltrating lymphocytes with enriched tumor-reactivity and specificity. Also disclosed is a method for treating a tumor in a subject that involves treating the subject with nonmyeloablative lymphodepleting chemotherapy, and administering tumor-infiltrating lymphocytes expanded by the disclosed methods.

15 Claims, 19 Drawing Sheets

(56) References Cited

U.S. PATENT DOCUMENTS

| | | |
|---|---|---|
| 9,844,569 B2 | 12/2017 | Gros et al. |
| 10,172,887 B2 | 1/2019 | Borrello et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2004/0209363 A1 | 10/2004 | Watts et al. |
| 2005/0106717 A1 | 5/2005 | Wilson et al. |
| 2011/0052530 A1 | 3/2011 | Dudley |
| 2011/0136228 A1 | 6/2011 | Vera et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2013/0302300 A1 | 11/2013 | Radvanyi et al. |
| 2014/0328791 A1 | 11/2014 | Bossard et al. |
| 2014/0377739 A1 | 12/2014 | Welch et al. |
| 2015/0175966 A1 | 6/2015 | Vera et al. |
| 2015/0320798 A1 | 11/2015 | Borrello et al. |
| 2016/0010058 A1 | 1/2016 | Gros et al. |
| 2016/0208216 A1 | 7/2016 | Vera et al. |
| 2016/0215262 A1 | 7/2016 | Powell |
| 2017/0044496 A1 | 2/2017 | Samaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |

FOREIGN PATENT DOCUMENTS

| | | |
|---|---|---|
| EP | 3188740 A1 | 7/2017 |
| WO | 9947690 | 9/1999 |
| WO | 2010042433 | 4/2010 |
| WO | 2011053322 | 5/2011 |
| WO | WO 2013/057500 A1 | 4/2013 |
| WO | 2013088147 | 6/2013 |
| WO | 2013173835 | 11/2013 |
| WO | 2013188427 | 12/2013 |
| WO | 2014133567 | 9/2014 |
| WO | 2015026684 | 2/2015 |
| WO | 2015189356 | 12/2015 |
| WO | 2015189356 A1 | 12/2015 |
| WO | 2015189357 | 12/2015 |
| WO | WO 2015/189357 A1 | 12/2015 |
| WO | WO 2016/053338 A1 | 4/2016 |
| WO | WO 2016/096903 A1 | 6/2016 |

OTHER PUBLICATIONS

Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

International Search Report and Written Opinion for International Patent Application No. PCT/US2018/012633 dated May 25, 2018, 11 pages.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Somerville RP, et al., "Clinical scale rapid expansion of lymphocytes for adoptive cell transfer therapy in the WAVE® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

European Patent Application No. 15776878.9, Examination Report dated Mar. 5, 2019, 4 Pages.

Ye et al.; Engineered artificial antigen presenting cells facilitate direct and efficient expansion of tumor infiltrating lymphocytes; Journal of Translational Medicine 2011, 9:131, 1-13.

Examination Report dated Jul. 29, 2020 for European Patent Application No. 15776878.9, 4 pages.

European Search Opinion for EP 15776878.9; dated Mar. 20, 2018; 2 pages.

Chacon J A, et al.; "Co-Stimulation through 4-1BB/CD137 Improves the Expansion and Function of CD8+ Melanoma Tumor-Infiltrating Lymphocytes for Adoptive T-Cell Therapy"; PLOS ONE, vol. 8, No. 4; Apr. 1, 2013.

Maclean H et al.; "Expansion of tumor-infiltrating lymphocytes (TIL) from human pancreatic tumors"; Journal for Immunotherapy of Cancer, vol. 4, No. 1, 61, Oct. 18, 2016.

Ott P A; "Immune Checkpoint Blockade in Cancer: Inhibiting CTLA-4 and PD-1/PD-L1 With Monoclonal Antibodies"; OncLive.com Feb. 21, 2014.

Mahmoud et al.; "Tumor-Infiltrating CD8+ Lymphocytes Predict Clinical Outcome in Breast Cancer"; J Clin. Oncol. 29 (15), 1949-1955, May 20, 2011.

Hernandez et al.; "Co-stimulation through the CD137/41BB pathway protects human melanoma tumor-infiltrating lymphocytes from activation-induced cell death and enhances anti-tumor effector function"; J Immunotherapy. 34(3), 236-250 Apr. 2011.

Wu et al., "Adoptive T-cell Therapy Using Autologous Tumom-infiltrating Lymphocytes for Metastatic Melanoma: Current Status and Future Outlook"; Cancer J. 18(2), 160-175, Mar./Apr. 2012.

Fisher, et al., "Targeting of 4-1BB by monoclonal antibody PF-05082566 enhances T-Cell function and tumor activity", Dancer Immunolog. & Immunother. 2012, 61, 1721-33.

Goff et al., "Tumor Infiltrating Lymphocyte Therapy for Metastatic Melanoma: Analysis of Tumors Resected for TIL", J. Immunother, Oct. 2010, 33(8), 840-847.

Lee et al., "Tumor-Infiltrating Lymphocytes in Melanoma", Curr Oncol Rep. Aug. 2012, 14, 468-474.

Vinay et al., "Dual Immunoregulatory pathways of 4-1BB Signaling", J. Mol Med., Feb. 2006, 84, 726-736.

Chang et al., "Emerging concepts in immunotherapy T-cell metabolism as a therapeutic target", Nat. Immunol., Apr. 2016, 17(4), 364-368.

Dudley, et al., "Cancer Regression and Autoimmunity in Patients After Clonal Repopulation with Antitumor Lymphocytes", Science, Oct. 2002, 298, 850-54.

Dudley, et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley, et al., "Adoptive Cell Therapy for Patients with Metastatic Melanoma: Evaluation of Intensive Myeloablative Chemoradiation Preparative Regimens", J. Clin. Oncol., Nov. 2008, 26(32), 5233-39.

Dudley, et al., "Generation of Tumor-Infiltrating Lymphocyte Cultures for USe in Adoptive Transfer Therapy for Melanoma Patients", J. Immunother., 2003, 26(4), 332-42.

(56) References Cited

OTHER PUBLICATIONS

Inozume et al., "Selection of CD8+PD-1+ Lymphocytes in Fresh Human Melanomas Enriches for Tumor-reactive T Cells", J Immounother, Nov.-Dec. 2010, 33(9), pp. 956-964.
Gross et al., "Selection of PD-1, LAG-3 and 41BB Positive CD8 T Cells in the Fresh Tumor Digest Enriches for Melanoma-Reactive Cells", J Immounother, Nov.-Dec. 2012, 35(9), pp. 721-723.
Kodumudi et al., "Immune Checkpoint Blockade to Improve Tumor Infiltrating Lymphocytes for Adoptive Cell Therapy", PLOS One, Apr. 2016, 13 pages.
Chacon et al., "Continuous 4-1BB co-stimulatory signals for the optimal expansion of tumor-infiltrating lymphocytes for adoptive T-cell therapy", Oncoimmunology 2013, 2(9):e25581.
Chacon et al., "Triggering co-stimulation directly in melanoma tumor fragments drives CD8+ tumor-infiltrating lymphocyte expansion with improved effector-memory properties", Oncoimmunology 2015, 4:12, e1040219.
Prieto, PA, Durflinger KH, Wunderlich JR, Rosenberg SA, and Dudley ME Enrichment of CD8+ cells from melanoma Tumor-infiltrating lymphocyte cultures reveals tumor reactivity for use in adoptive cell therapy. (2010) J Immunother 33 (5): 547-56.
Wu, et al., "Adoptive T-Cell Therapy Using Autologous Tumor-Infiltrating Lymphocytes for A51 Metastatic Melanoma: Current Status and Future Outlook", CancerJ. 2012, vol. 18(2), p. 160-175.
Chacon et al., "Manipulating the Tumor Microenvironment Ex Vivo for Enhanced Expansion of Tumor-Infiltrating Lymphocytes for Adoptive Cell Therapy", Clinical Cancer Research, Feb. 1, 2015 21(3), pp. 611-621.
Teschner et al., "In Vitro Stimulation and Expansion of Human Tumour-Reactive CD8+ Cytotoxic T Lymphocytes by Anti-CD3/CD28/CD137 Magnetic Beads", Scandinavian Journal of Immunology, Aug. 2011, 74(2), pp. 155-164.
European Patent Application No. 15776878.9, Extended European Search Report, dated Mar. 20, 2018, 7 pages.
Hall et al., "Expansion of Tumor-Infiltrating Lymphocytes (TIL) from Human Pancreatic Tumors", Journal for ImmunoTherapy of Cancer, Oct. 2016, 4(61), 12 pages.
Benencia, F, et al. Dendritic cells the tumor microenvironment and the challenges for an effective antitumor vaccination. (2011) J Biomed Biotechnol 2012:425476.
Besser, MJ, et al. Minimally cultured or selected autologous tumor-infiltrating lymphocytes after a lympho-depleting chemotherapy regimen in metastatic melanoma patients. (2009) J Immunother 32(4):415-23.
Besser, MJ, et al. Clinical responses in a phase II study using adoptive transfer of short-term cultured tumor infiltration lymphocytes in metastatic melanoma patients. (2010) Clin Cancer Res 16(9):2646-55.
Engelhardt, JJ, et al. Marginating dendritic cells of the tumor microenvironment cross-present tumor antigens and stably engage tumor-specific T cells (2012) Cancer Cell 21 (3):402-17.
Friedman, KM, et al. Tumor-specific CD4+ melanoma tumor-infiltrating lymphocytes. (2012) J Immunother 35(5):400-8.
Ghattas, I. R. et al., The encephalomyocarditis virus internal ribosome entry site allows efficient coexpression of two genes from a recombinant provirus in cultured cells and in embryos. (1991) Mol. Cell. Biol., 11 :5848-5849.
Powell, DJ, et al. Transition of late-stage effector T cells to CD27+ CD28+ tumor-reactive effector memory T cells in humans after adoptive cell transfer therapy. (2005) Blood 105(1):241-50.
Hershkovitz, L, et al Focus on adoptive T cell transfer trials in melanoma. (2010) Clin Dev Immunol 2010:260267.
Huang, J, et al Modulation by IL-2 of CD70 and CD27 expression on CD8+ T cells: importance for the therapeutic effectiveness of cell transfer immunotherapy (2006) J Immunol 176(12):7726-35.
Ichii, H, et al Role for Bcl-6 in the generation and maintenance of memory CD8+ T cells. (2002) Nat Immunol 3 (6):558-63.
Ichii, H, et al Bcl6 acts as an amplifier for the generation and proliferative capacity of central memory CD8+ T cells. (2004) J Immunol 173(2):883-91.

International Search Report and Written Opinion issued in International Application No. PCT/US15/25313 dated Jul. 9, 2015.
Itzhaki, O, et al Establishment and large-scale expansion of minimally cultured "young" tumor infiltrating lymphocytes for adoptive transfer therapy. (2011) J Immunother 34(2):212-20.
Kim, JO, et al NF-kappaB and AP-1 regulate activation-dependent CD137 (4-1BB) expression in T cells. (2003) FEBS Lett 541 (1-3): 163-70.
Li, G, et al T-Bet and Eomes Regulate the Balance between the Effector/Central Memory T Cells versus Memory Stem Like T Cells. (2013) PLoS One 8(6):e67401.
Lynch, DH (2008) The promise of 4-1 BB (CD137)-mediated immunomodulation and the immunotherapy of cancer. Immunol Rev 222: 277-86.
Ma, Y, et al Dendric Cells in the Cancer Microenvironment. (2013) J Cancer 4(1 ):36-44.
Macejak and Sanow, Internal initiation of translation mediated by the 5' leader of a cellular mRNA. (1991) Nature, 353:91.
Pilon-Thomas, S, et al. Blockade of programmed death ligand 1 enhances the therapeutic efficacy of combination immunotherapy against melanoma. (2010) J Immunol 184(7): 3442-9.
Melero, I, Hirschhom-Cymerman D, Morales-Kastresana A, Sanmamed MF, and Wolchok JD. Agonist antibodies to FNFR molecules that costimulate T and NK cells. (2013) Clin Cancer Res 19(5): 1044 53.
Mountford PS, Smith AG. Internal ribosome entry sites and dicistronic RNAs in mammalian transgenesis. Trends Genet. May 1995; 11 (5):179-84.
Oh et al., Homeotic gene Antennapedia mRNA contains 5'-noncoding sequences that confer translational initiation by internal ribosome binding. (1992) Genes & Development, 6:1643-1653.
Peng, W, et al. PD-1 blockade enhances T-cell migration to tumors by elevating IFN-y inducible chemokines. (2012) Cancer Res 72(20):5209-18.
Pearce, EL, et al Control of effector CD8+ T cell function by the transcription factor Eomesodermin. (2003) Science 302(5647):1041-3.
Pelletier and Sonenberg. Internal initiation of translation of eukaryotic mRNA directed by a sequence derived from poliovirus RNA. Nature, 334:320325 (1988).
Radvanyi, LG, et al. Specific lymphocyte subsets predict response to adoptive cell therapy using expanded autologous tumor-infillrating lymphocytes in metastatic melanoma patients. (2012) Clin Cancer Res 18(24):6758-70.
Rosenberg, SA, et al. A new approach to the adoptive immunotherapy of cancer with tumorinfiltrating lymphocytes. (1986) Science 233(4770):1318-21.
Rosenberg, SA, et al. Use of tumor-infiltrating lymphocytes and interleukin-2 in the immunotherapy of patients with metastatic melanoma. A preliminary report. (1988) N Engl J Med 319(25)1676-80.
Rosenberg, SA, et al. Adoptive cell transfer: a clinical path to effective cancer immunotherapy. (2008) Nat Rev Cancer 8(4):299-308.
Scheeren, FA, et al. STAT5 regulates the self-renewal capacity and differentiation of human memory B cells and controls Bcl-6 expression. (2005) Nat Immunol 6(3): 303-13.
Topalian, SL, et al. Survival, durable tumor remission, and long-term safety in patients with advanced melanoma receiving nivolumab. (2014) J Clin Oncol 32:1020-1030.
Tran, KQ, et al. Minimally cultured tumor-infiltrating lymphocytes display optimal characteristics for adoptive cell therapy. (2008) J Immunother 31 (8):742-51.
Valkenburg, SA, et al. Protective efficacy of cross-reactive CD8+ T cells recognising mutant viral epitopes depends on peptide-MHC-1 structural interactions and T cell activation threshold. (2010) PLoS Pathog 6(8) e1001039.
Watts, TH (2005) TNF/TNFR family members in costimulation of T cell responses. Annu Rev Immunol 23: 23-68.
Ye, Q, et al. CD 137 accurately identifies and enriches for naturally occurring tumor-reactive T cells in tumor. (2013) Clin Cancer Res 20(1):44-55.
Yoshida, K, et al. Bcl6 controls granzyme B expression in effector CD8+ T cells. (2006) Eur J Immunol 36(12):3146-56.

(56) References Cited

OTHER PUBLICATIONS

Written Opinion dated Jul. 9, 2015 for International Patent Application No. PCT/US2015/025313, 6 pages.
International Search Report dated Jul. 9, 2015 for International Patent Application No. PCT/US2015/025313, 3 pages.
Dudley, ME. Adoptive cell therapy for patients with melanoma. (2011) J Cancer 2:360-2.
European Exam Report for EP 15776878.9; dated Jul. 23, 2021; 5 pages.

* cited by examiner

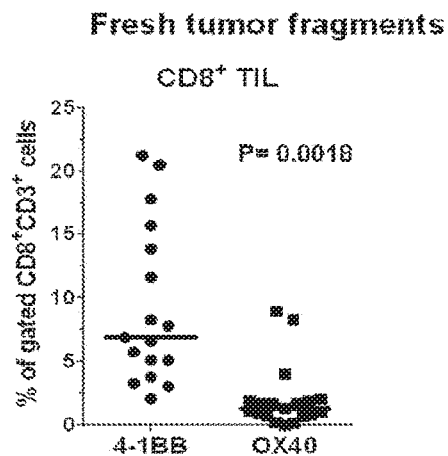
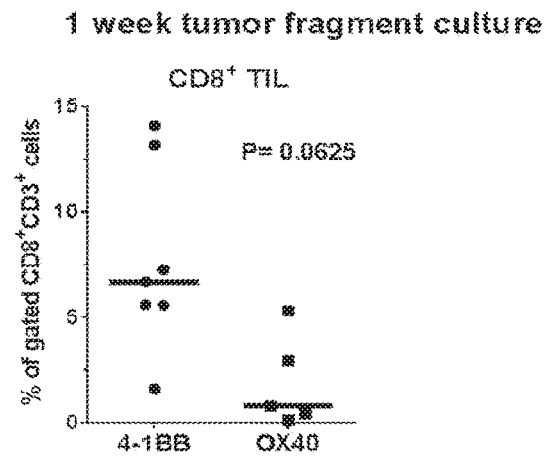
FIGURE 1A
FIGURE 1B
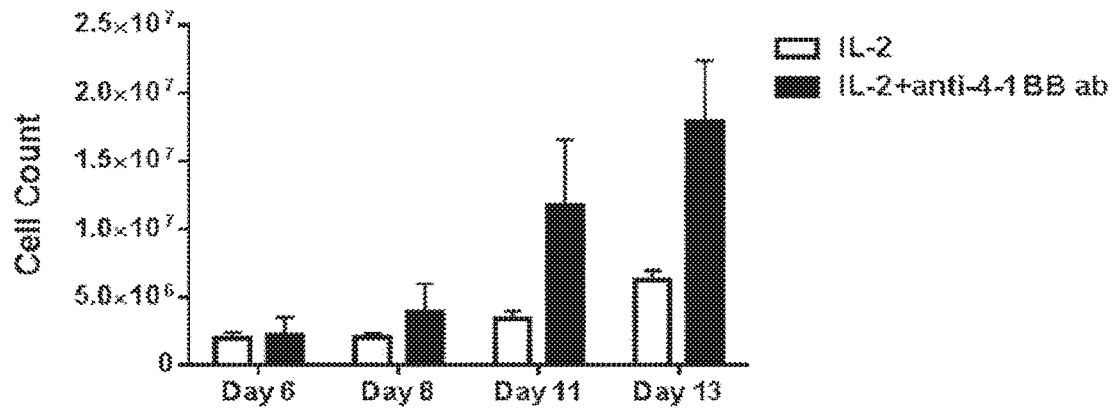
FIGURE 2A

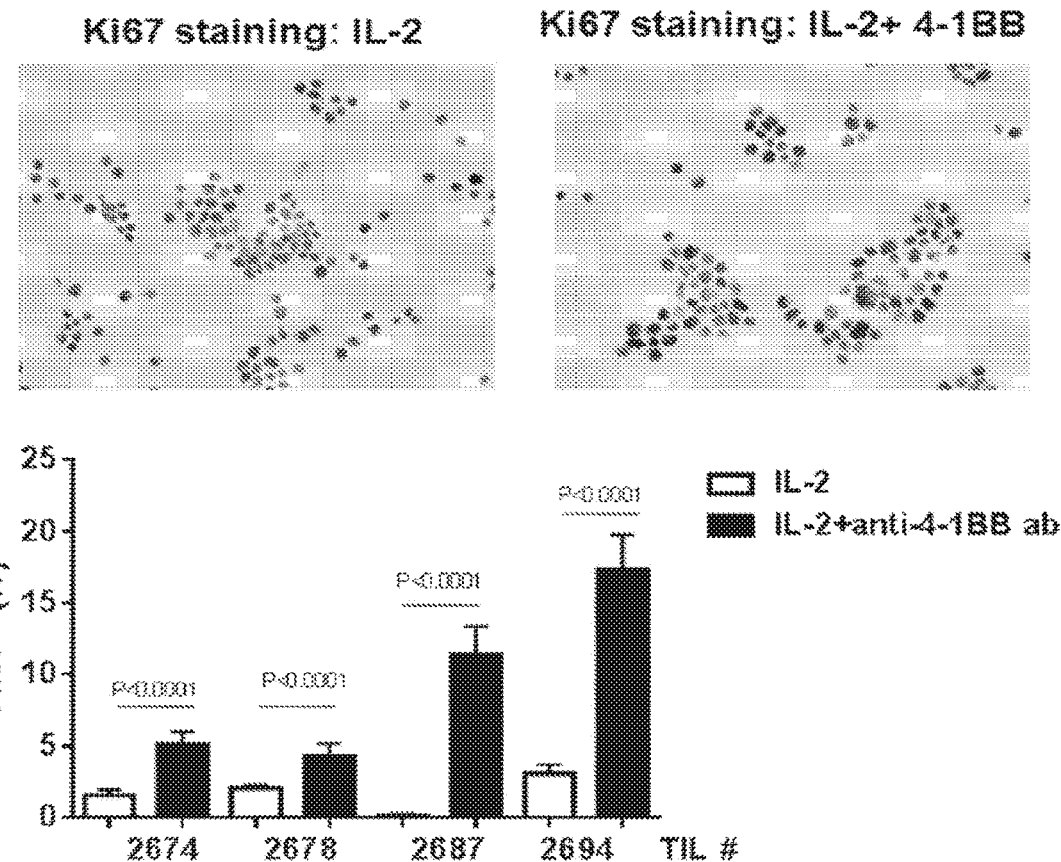
*FIGURE 2B*
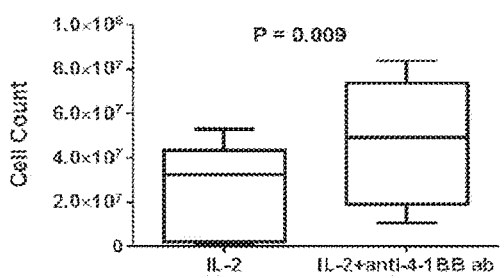
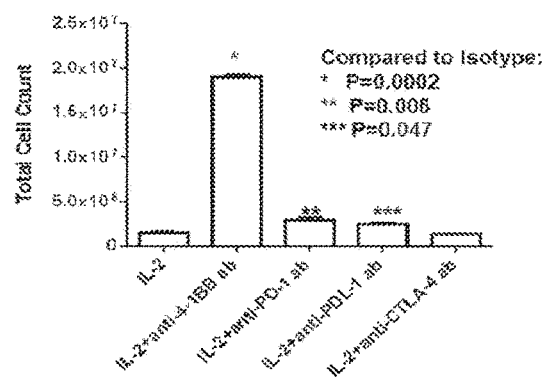
*FIGURE 2C*          *FIGURE 2D*

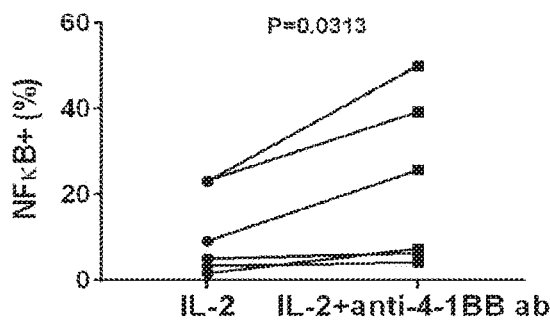
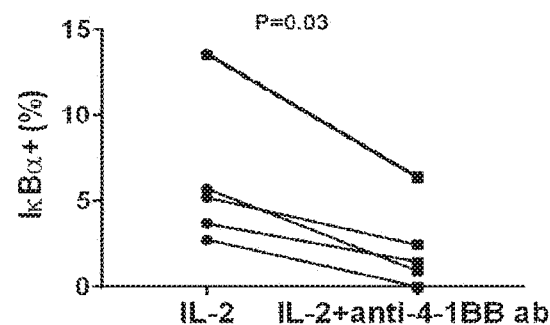
*FIGURE 3C*  *FIGURE 3D*
TIL 2678
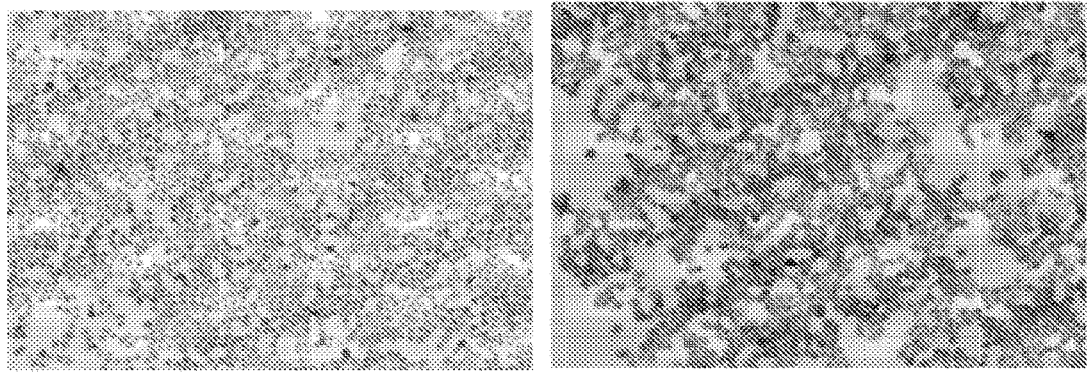
*FIGURE 4A*
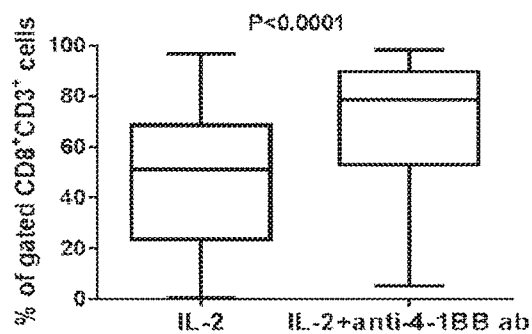
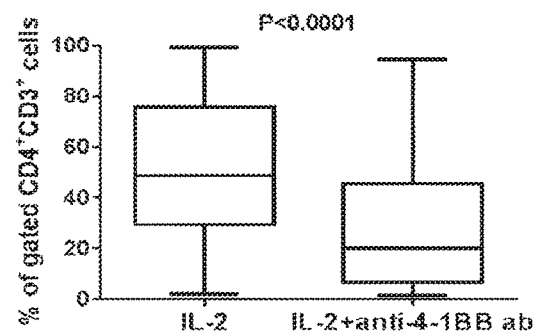
*FIGURE 4B*  *FIGURE 4C*

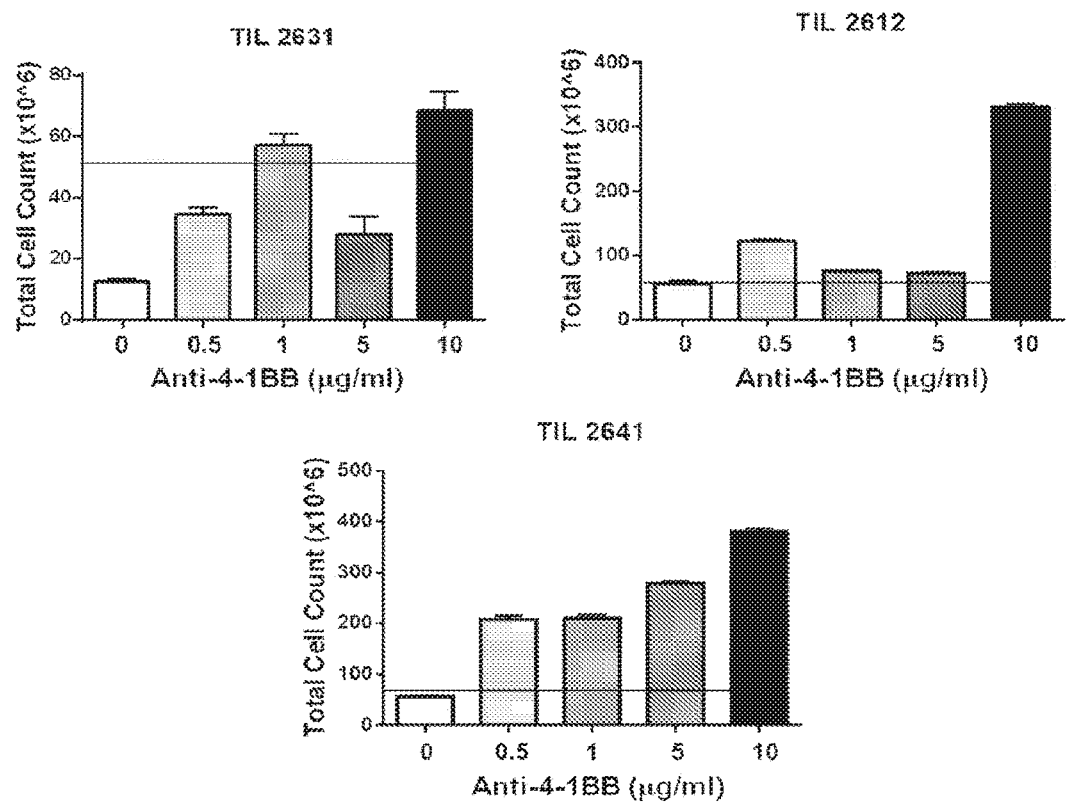
*FIGURE 8*
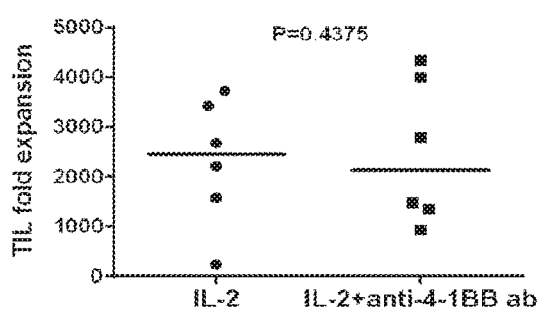
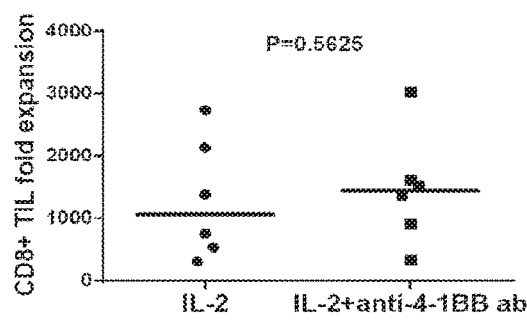
*FIGURE 9A*  *FIGURE 9B*

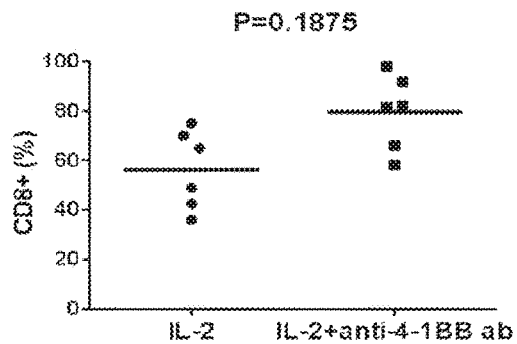
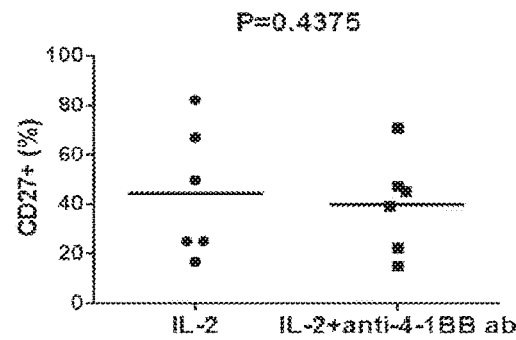
FIGURE 9C          FIGURE 9D
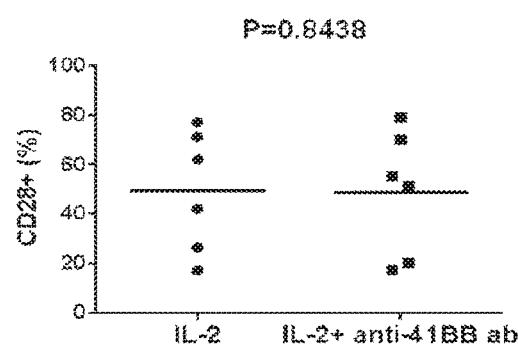
FIGURE 9E
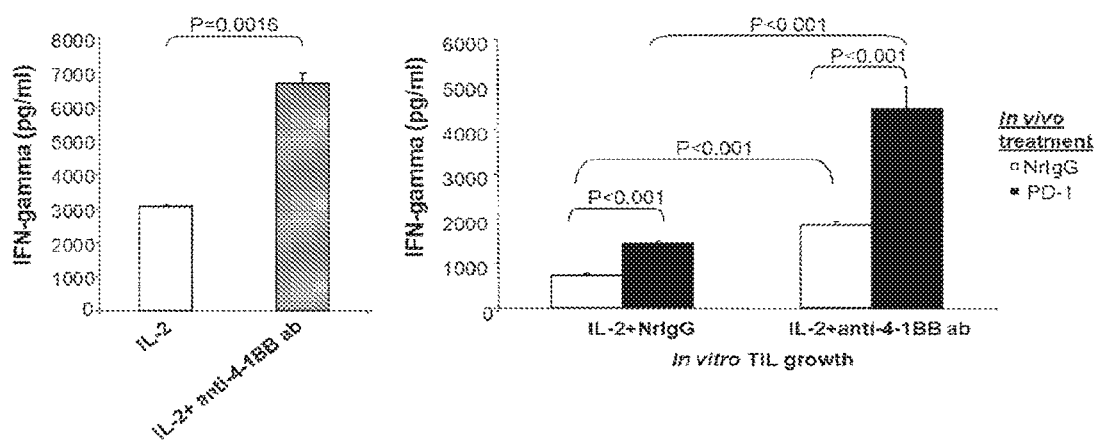
FIGURE 10A          FIGURE 10B

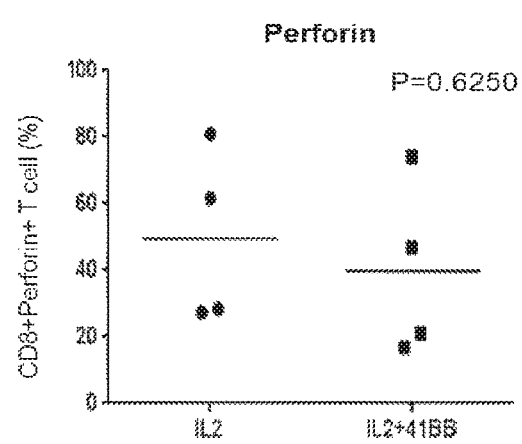 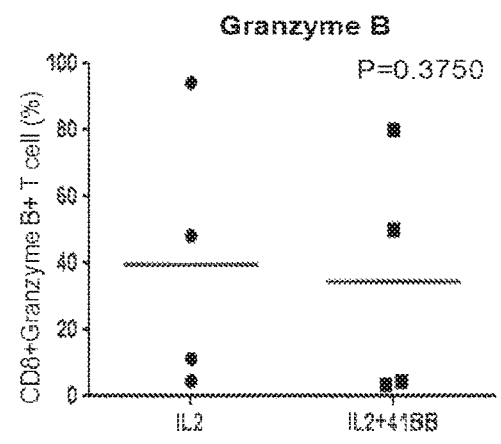
*FIGURE 19A*  *FIGURE 19B*

ENHANCED EXPANSION OF TUMOR-INFILTRATING LYMPHOCYTES FOR ADOPTIVE CELL THERAPY

CROSS-REFERENCE TO RELATED APPLICATIONS

The present application is a continuation of U.S. patent application Ser. No. 15/303,201 filed Oct. 10, 2016, which is a U.S. National Stage Application of PCT/US2015/025313 filed Apr. 4, 2015, which claims benefit of U.S. Provisional Application No. 61/978,112 filed Apr. 10, 2014, all of which are incorporated herein by reference in their entireties.

BACKGROUND

T-cell-based therapies have emerged to be powerful mediators of anti-tumor responses in both liquid and solid tumors [Dudley, M E (2011) J Cancer 2:360-2; Rosenberg, S A, et al (2008) Nat Rev Cancer 8(4):299-308]. Over the past 3 decades, accumulating evidence has demonstrated the potential of treating metastatic melanoma patients with their own tumor-infiltrating lymphocytes (TILs) as a form of personalized therapy [Dudley, M E (2011) J Cancer 2:360-2; Rosenberg, S A, et al (2008) Nat Rev Cancer 8(4):299-308; Radvanyi, L G, et al (2012) Clin Cancer Res 18(24):6758-70]. Adoptive cell therapy (ACT) with TILs for melanoma is predicated on the enriched tumor antigen-specificity of T cells infiltrating tumors which can be expanded to high numbers and re-infused. The protocol used in most centers involves the initial outgrowth of TILs from 4-6 $mm^2$ cut fragments from metastatic melanoma surgical resections or biopsies using IL-2 as a growth factor [Dudley, M E (2011) J Cancer 2:360-2; Rosenberg, S A, et al (2008) Nat Rev Cancer 8(4):299-308; Radvanyi, L G, et al (2012) Clin Cancer Res 18(24):6758-70]. These initial tumor fragment cultures usually take about 3-5 weeks to yield enough TILs for secondary expansion in a larger scale to yield the final infusion product. Although earlier clinical trials were not that encouraging, the introduction of a non-myeloablative transient lymphodepleting chemotherapy regimen before adaptive transfer of autologous TILs expanded ex vivo has significantly boosted clinical response rates to around 45-50% [Rosenberg, S A, et al (1988) N Engl J Med 319(25):1676-80; Rosenberg, S A, et al (1986) Science 233(4770):1318-21]. Phase II clinical trials in a number of TIL therapy centers around the world using this general approach of tumor fragment-derived TIL has reproduced these results and long-term follow-up of patients treated with their own TIL is now also showing a survival benefit over other conventional therapies, especially in patients that have progressed even after other immunotherapies such as IL-2, anti-CTLA-4, and anti-PD-1 [Dudley, M E (2011) J Cancer 2:360-2; Rosenberg, S A, et al (2008) Nat Rev Cancer 8(4):299-308; Radvanyi, L G, et al (2012) Clin Cancer Res 18(24):6758-70; Besser, M J, et al (2010) Clin Cancer Res 16(9):2646-55].

$CD8^+$ TILs enriched in tumor specificity have emerged to be critical in mediating tumor regression in a number of Phase II TIL trials, and current efforts are now aimed to not only increase the expansion of $CD8^+$ T cells from tumor tissue, but also increase the anti-tumor activity and effector-memory phenotype of the final TIL infusion product to improve persistence after adoptive transfer [Dudley, M E (2011) J Cancer 2:360-2; Rosenberg, S A, et al (2008) Nat Rev Cancer 8(4):299-308; Radvanyi, L G, et al (2012) Clin Cancer Res 18(24):6758-70; Besser, M J, et al (2010) Clin Cancer Res 16(9):2646-55; Valkenburg, S A, et al (2010) PLoS Pathog 6(8)]. In addition, accelerating the rate of TIL expansion from the initial tumor fragment cultures has also become a priority to minimize the time the cells are in culture and shorten the time from surgery to treatment and prevent patient protocol withdrawal, especially when contemplating out-scaling TIL manufacturing to larger cohorts of patients [Besser, M J, et al (2010) Clin Cancer Res 16(9):2646-55; Tran, K Q, et al (2008) J Immunother 31(8):742-51; Besser, M J, et al (2009) J Immunother 32(4):415-23; Itzhaki, O, et al (2011) J Immunother 34(2): 212-20].

Metastatic melanomas contain a population of $CD8^+$ T cells expressing activation markers, such as PD-1 and 4-1BB/CD137, indicating a recent history of antigenic stimulation in the tumor microenvironment in vivo [Ye, Q, et al (2013) Clin Cancer Res 20(1):44-55]. Recent studies have found that $CD8^+$ TIL expressing 4-1BB especially, represent the most highly enriched tumor-specific sub-population of T cells in melanoma [Ye, Q, et al (2013) Clin Cancer Res 20(1):44-55]. Protocols are now being developed to purify $4-1BB^+$ $CD8^+$ T cells from melanoma tissues and expand these selected cells for infusion. Although this approach is promising, it has a number of caveats, including the need to prepare single cell suspensions from tumor tissues, the variable and sometimes low frequency of $4-1BB^+$ T cells in tumors that can make positive selection methods difficult, the small sizes of tumor tissue available in many cases from biopsies of surgical resections that yield few cells after enzymatic digestion or mechanical disaggregation, and the possibility that not all tumor-specific $CD8^+$ T cells may be in an activated ($4-1BB^+$) state at the time the tumor was taken out and processed for TIL expansion.

SUMMARY

Disclosed herein is a method for ex vivo expanding tumor-infiltrating lymphocytes for use in adoptive cell therapy (ACT). The method involves culturing tumor fragments from the subject in a culture medium containing IL-2 and a 41BB agonist in an amount effective to expand tumor-infiltrating lymphocytes with enriched tumor-reactivity and specificity. For example, the method can enrich for tumor-specific CD8' TILs compared to IL-2 alone. This increased tumor specificity can in some cases be maintained after further secondary rapid expansion (REP) with, for example, anti-CD3, irradiated PBMC feeder cells, and IL-2. Also disclosed is a method for treating a tumor in a subject that involves treating the subject with nonmyeloablative lymphodepleting chemotherapy, and administering tumor-infiltrating lymphocytes expanded by the disclosed methods.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 1A and 1B are plots showing detection of 4-1BB on CD8' T cells within melanoma tumor metastases and after 1 week of tumor fragment culture. Using flow cytometry, the expression of 4-1BB and OX40 was measured on CD8+ TIL single cell suspensions from 18 freshly-isolated melanoma metastasis (FIG. 1A) and tumor fragment cultures after 1 week from 7 patients (FIG. 1B).

FIGS. 2A to 2C show that anti-4-1BB agonistic antibody increases TIL expansion in vitro. Melanoma tumors were surgically resected from patients. The tumors were then cut up into multiple fragments and placed in culture with IL-2±anti-4-1BB antibody. Cell counts were conducted from days 6-14 using a hemocytometer and Trypan Blue. At these early time points, the 4-1BB activated TIL grew faster compared to the IL-2 control (FIG. 2A). When determining the proliferation of the TIL at early time points, an increased expression of Ki67 proliferation marker was found in the 4-1BB activated TIL as compared to the control as demonstrated using immunocytochemistry (FIG. 2B top) and further demonstrated in 4 independent TIL lines in the quantification data (FIG. 2B bottom). Using a hemocytometer and Trypan Blue, viable cell counts were determined after 3 weeks in culture, showing that the TIL expanded with the anti-4-1BB antibody expanded better than the IL-2 control (FIG. 2C). After 3 weeks in culture with IL-2 and different antibodies (anti-4-1BB, anti-PD-1, anti-PDL-1, anti-CTLA-4 or IL-2 alone), cell counts were conducted using a hemocytometer after Trypan Blue staining. The TTL grown with the agonistic anti-4-1BB antibody exhibited the most TIL expansion as compared to the other antibodies (FIG. 2D).

FIGS. 3A to 3D show increased NFκB translocation in TIL expanded with the anti-4-1BB antibody. Melanoma tumors were cut up into multiple fragments and placed in culture with IL-2 and with or without an anti-4-1BB antibody. After 1 week, the cells were collected and cytospin and Immunocytochemistry were done. Staining for NFκB (p65) revealed more translocation in the nucleus of TIL grown with IL-2 and the anti-4-1BB antibody compared to TIL grown with IL-2 alone. Vectra Intelligents slide analysis system (Nuance software) (FIG. 3A) was used to observe the translocation of NFκB (red is nucleus; green is NFκB; and yellow is overlay (translocation)). The arrows indicate areas where translocation occurred. Quantification of NFκB translocation in 10 different areas per sample is demonstrated in 3 independent TIL samples (FIG. 3B). The percentage of NFκB and IκBα expression was also measured in the TIL within the fragment after 1 week in culture using flow cytometry (FIG. 3C, 3D). The fragments were set up with or without the addition of anti-4-1BB antibody with IL-2 or with IL-2 alone. After 1 week, the fragment was collected and mechanically disaggregated using glass slides. The cells were filtered and stained using flow cytometry. The TIL were gated on live, $CD3^+$, $CD8^+$ TIL and the percentage of NFκB (FIG. 3C) and IκBα (FIG. 3D) was measured. The TIL cultured with IL-2 plus anti-4-1BB antibody exhibited an increase NFκB (FIG. 3C) with a paralleled decrease in IκBα (FIG. 3D).

FIGS. 4A to 4D show that CD8" TIL percentage is increased with the addition of anti-4-1BB antibody to TIL cultures. Experiments were conducted to determine whether activating the 4-1BB pathway could augment the percentage of $CD8^+$ TIL in the cultures. 1 week after the fragments were set up, immunocytochemistry was conducted, revealing that the TIL expanded with IL-2 and anti-4-1BB antibody exhibited an increase in $CD8^+$ cells, as shown in one representative TIL line (FIG. 4A). After being in culture for 3 weeks, the TILs were stained for the expression of CD3, CD8, and CD4 using flow cytometry. In 56 independent TIL lines grown with TL-2 and anti-4-1BB antibody the percentage of $CD8^+$ TTL increased in the CD3 subset compared to the IL-2 control (FIG. 4B). When the $CD4^+$ expression was examined in the 56 independent TIL lines, the TILs expanded with IL-2 alone exhibited an increase in $CD4^+$, compared to TIL grown with IL-2 plus anti-4-1BB antibody (FIG. 4C). Since the IL-2 control had an increased percentage of $CD4^+$ TIL (FIG. 4C), the percentage of T regulatory cells (Tregs) was examined. The control TIL (IL-2) exhibited an increased percentage of Tregs then the TIL expanded in anti-4-1BB antibody (FIG. 4D).

FIG. 8 is a bar graph showing dose titration of different concentrations of agonist anti-4-1BB antibody added to melanoma tumor fragment cultures to determine the optimal dose for the anti-4-1BB antibody for initial TIL expansion. Cells counts were done after 3 weeks of culture of the tumor fragments with or without the indicated concentrations of anti-4-1BB (BMS 663513). 10 mg/ml anti-4-1BB antibody was found to optimal and induced the highest TIL expansion in initial experiments on 3 different melanoma patient tumors (5 fragments per condition for each anti-41-BB dose).

FIGS. 9A to 9E show that TILs initially expanded with anti-4-1BB antibody continue to expand during secondary expansion. After TIL were initially expanded with or without anti-4-1BB antibody, the pre-REP TIL, were then subjected to the REP. After the 2 week expansion, phenotype analysis and cell counts were conducted. Post-REP TIL initially expanded with anti-4-1BB antibody exhibited increased CDR' expression (FIG. 9A) and similar levels of CD27 (FIG. 9B) and CD28 (FIG. 9C). Total (FIG. 9D) and CD8 (FIG. 9E) fold expansion was not disrupted despite the loss of CD27 at the pre-REP level in the TIL expanded with anti-4-1BB antibody.

FIGS. 10A and 10B are bar graph showing that addition of anti-4-1BB antibody during ex vivo expansion of TIL isolated from B16 melanomas increases anti-tumor reactivity. Mice were injected subcutaneously with $1 \times 10^5$ B16 melanoma cells. Tumors were resected on day 21, digested, and T cells were purified by AUTOMACS separation. T cells were cultured in vitro with 6000 TU/ml IL-2 or IL-2 plus anti-4-1BB for 7 days. T cells from B16 tumors were co-cultured with B16 cells (FIG. 10A). Supernatants were collected and IFN-gamma was measured by ELISA. Beginning on day 3 after B16 tumor injection and continuing every 3-4 days after, mice received i.p. 20 mg/kg normal or non-specific IgG (NrIgG) or anti-PD1 antibody. Tumors were resected, digested and T cells were purified by AUTOMACS (Miltenyi) separation. T cells were cultured in vitro with 6000 TU/ml TL-2 and 10 mg/ml NrIgG or anti-4-1BB antibody. On day 7, T cells were co-cultured with B16 cells for 24 hours. Supernatants were collected and IFN-gamma was measured by ELISA (FIG. 10B).

FIGS. 19A to 19B show Perforin and Granzyme B expression in CD8+ TIL expanded from tumor fragments with or without added anti-4-1BB.

DETAILED DESCRIPTION

Figure 3A:
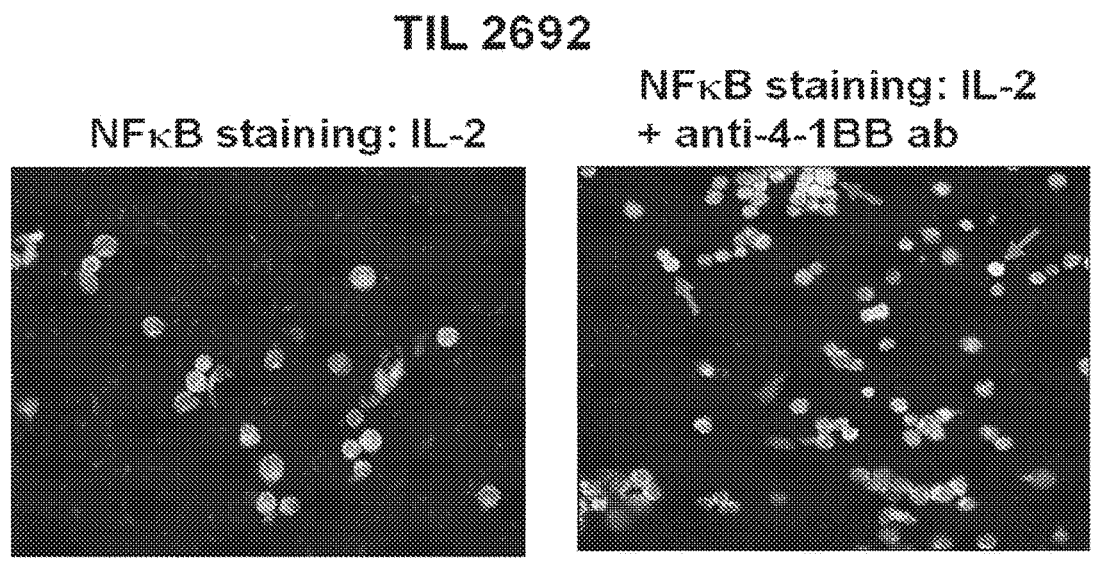

Disclosed are compositions and methods to directly manipulate co-stimulatory pathways within the initial melanoma tumor fragment cultures to capitalize on the de novo expression of co-stimulatory molecules due to previous antigenic stimulation on resident $CD8^+$ T cells. This approach can accelerate the rate of TIL expansion out of the tumor fragments and enrich the tumor-specific T cells at the same time. Moreover, additional antigenic stimulation that occurs during the early tumor fragment culture from antigen presentation can induce further T-cell co-stimulatory molecule expression that can be further used to enhance T-cell outgrowth. Tumor fragments have been used for years to expand TIL by simply adding exogenous IL-2, but whether other immunomodulators can be added in these tumor fragment cultures to affect TIL expansion and phenotype has basically been ignored.

As disclosed herein, the 4-1BB co-stimulatory pathway can be exploited in melanoma tumor fragment cultures in an active rather than a passive way by activating 4-1BB signaling using a 4-1BB agonist to enhance the output of $CD8^+$ T cells, their tumor reactivity, and memory properties to develop a practical way to improve the TIL therapy product. 4-1BB expression can be seen on resident CD8+ T cells in melanoma metastases and is maintained during the culture of tumor fragments for at least a week in a significant frequency of CD8+ T cells in these early cultures ex vivo. The effects of an agonistic anti-4-1BB antibody added during the initiation of individual tumor fragment cultures was tested, and as disclosed herein, this increased the rate of CD8+ TIL expansion as well as the tumor reactivity of the expanded product. 4-1BB co-stimulation during these early tumor fragment cultures also induced the expression of survival signaling pathways (NFκB) in CD8+ TIL as well as the expression of anti-apoptotic and T-cell memory genes. Other possible mechanisms of action were also examined, revealing that resident dendritic cells (DC) in the tumor fragments survive for considerable periods of time and also express 4-1BB. These tumor fragment resident DC also activate NFκB, and up-regulate certain maturation markers with 4-1BB agonist addition. In addition, experiments were conducted to determine whether ongoing HLA class I antigen presentation occurs in the early tumor fragment cultures that may enhance the output of CD8+ TIL. Addition of a blocking anti-HLA class I antibody was shown to reduce the output of CD8+ TIL, especially with anti-4-1BB, suggesting that continual antigen presentation occurs ex vivo in these early tumor fragment cultures that was not considered before.

TIL Expansion

Tumor-infiltrating lymphocyte (TIL) production is a 2-step process: 1) the pre-REP (Rapid Expansion) stage where you the grow the cells in standard lab media such as RPMI and treat the TILs w/reagents such as irradiated feeder cells, and anti-CD3 antibodies to achieve the desired effect; and 2) the REP stage where you expand the TILs in a large enough culture amount for treating the patients. The REP stage requires cGMP grade reagents and 30-40 L of culture medium. However, the pre-REP stage can utilize lab grade reagents (under the assumption that the lab grade reagents get diluted out during the REP stage), making it easier to incorporate alternative strategies for improving TIL production. Therefore, in some embodiments, the disclosed TLR agonist and/or peptide or peptidomimetics can be included in the culture medium during the pre-REP stage.

ACT may be performed by (i) obtaining autologous lymphocytes from a mammal, (ii) culturing the autologous lymphocytes to produce expanded lymphocytes, and (ii) administering the expanded lymphocytes to the mammal. Preferably, the lymphocytes are tumor-derived, i.e. they are TILs, and are isolated from the mammal to be treated, i.e. autologous transfer.

Autologous ACT as described herein may also be performed by (i) culturing autologous lymphocytes to produce expanded lymphocytes; (ii) administering nonmyeloablative lymphodepleting chemotherapy to the mammal; and (iii) after administering nonmyeloablative lymphodepleting chemotherapy, administering the expanded lymphocytes to the mammal. Autologous TILs may be obtained from the stroma of resected tumors. For this, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase).

Expansion of lymphocytes, including tumor-infiltrating lymphocytes, such as T cells can be accomplished by any of a number of methods as are known in the art. For example, T cells can be rapidly expanded using non-specific T-cell receptor stimulation in the presence of feeder lymphocytes and interleukin-2 (IL-2), IL-7, IL-15, IL-21, or combinations thereof. The non-specific T-cell receptor stimulus can e.g. include around 30 ng/ml of OKT3, a mouse monoclonal anti-CD3 antibody (available from Ortho-McNeil®, Raritan, N.J. or Miltenyi Biotec, Bergisch Gladbach, Germany). Alternatively, T cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, e.g., approximately 0.3 µM MART-1:26-35 (27 L) or gp100:209-217 (210M)), in the presence of a T-cell growth factor, such as around 200-400 Ill/ml, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

Specific tumor reactivity of the expanded TILs can be tested by any method known in the art, e.g., by measuring cytokine release (e.g., interferon-gamma) following co-culture with tumor cells. In one embodiment, the autologous ACT method comprises enriching cultured TILs for CD8+ T cells prior to rapid expansion of the cells. Following culture of the TILs in IL-2, the T cells are depleted of CD4+ cells and enriched for CD8+ cells using, for example, a CD8 microbead separation (e.g., using a CliniMACS<plus>CD8 microbead system (Miltenyi Biotec)). In some embodiments, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

4-1BB Agonists

The disclosed results indicate that tumor fragments placed in culture to expand TIL for adoptive cell therapy are not static tissues, but small, dynamic tumor microenvironments that can be manipulated to alter the yield and phenotype of TILs being expanded for cell therapy as well as enrich for tumor reactivity and improved memory phenotype. 4-1BB co-stimulation enhancement in this system can manipulate these ex vivo tumor microenvironments to expand optimally active TIL for adoptive cell therapy.

Therefore, disclosed herein is a method for ex vivo expanding tumor-infiltrating lymphocytes for use in adoptive cell therapy (ACT). The method involves culturing tumor fragments from the subject in a culture medium containing IL-2 and a 41BB agonist in an amount effective to expand tumor-infiltrating lymphocytes with enriched tumor-reactivity and specificity. The culture medium can further contain a checkpoint inhibitor, such as anti-PD-1 antibody (e.g., BMS 936558), anti-PD-L1 antibody (e.g., cloneM1H1), anti-CTLA-4 antibody (e.g., Ipilimumab, BMS), or any combination thereof.

Also disclosed is a method for treating a tumor in a subject that involves treating the subject with nonmyeloablative lymphodepleting chemotherapy, and administering tumor-infiltrating lymphocytes expanded by the disclosed methods.

4-1BB Ligand

The 4-1BB glycoprotein is a member of the tumor necrosis factor receptor superfamily and binds to a high-affinity ligand (4-1BBL) expressed on several antigen-presenting cells such as macrophages and activated B cells. Therefore, in some embodiments, the 4-1BB agonist is a 4-1BBL protein, or a fragment or variant thereof capable of ligating 4-1BB on T-cell.

In some embodiments, the 4-1BB agonist is a recombinant protein, such as recombinant human 4-1BB. The recombinant protein can have the native 4-1BBL sequence. An example protein sequence for human 4-1BBL is provided in UniProtKB/Swiss-Prot Accession No. P41273. However, the recombinant protein can also be a fragment, variant, or combination thereof so long as it is capable of ligating 4-1BB on T-cell.

In some embodiments, the recombinant protein is a fusion protein. Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography). Chimeric proteins can also be manufactured with toxins or anti-bodies attached to them in order to study disease development.

Alternatively, internal ribosome entry sites (IRES) elements can be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781). IRES sequences arc known in the art and include those from encephalomyocarditis virus (EMCV) (Ghattas, I. R. et al., Mol. Cell. Biol., 11:5848-5849 (1991); BiP protein (Macejak and Sarnow, Nature, 353:91 (1991)); the Antennapedia gene of drosophilia (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)).

Antibodies

In some embodiments, the 4-1BB agonist is an agonistic anti-4-1BB antibody capable of ligating 4-1BB on T-cells to induce its co-stimulatory activity. Suitable antibodies include both polyclonal and monoclonal antibodies. Antibodies that can be used in the disclosed compositions and methods include whole immunoglobulin (i.e., an intact antibody) of any class, fragments thereof, and synthetic proteins containing at least the antigen binding variable domain of an antibody.

The disclosed antibody can be a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Currently, a humanized anti-4-1BB antibody is in clinical trials in patients with solid tumors, including melanoma, renal carcinoma, and ovarian cancer, and so far seems to have a favorable toxicity profile.

There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively. The disclosed antibody can be of any of these classes so long as it is able to ligate 4-1BB on T-cells.

Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (1), based on the amino acid sequences of their constant domains. Depending on the amino acid sequence of the constant domain of their heavy chains, immunoglobulins can be assigned to different classes.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules.

The antibodies can also be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

In vitro methods are also suitable for preparing monovalent antibodies. Digestion of antibodies to produce fragments thereof, particularly, Fab or F(ab)$_2$ fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields an Fc fragment and an F(ab)$_2$ fragment that has two antigen combining sites and is still capable of cross-linking antigen.

Aptamers

In some embodiments, the 4-1BB agonist is an agonistic aptamer capable of ligating 4-1BB on T-cells to induce its co-stimulatory activity. The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

Nucleic acid aptamers are typically oligonucleotides ranging from 15-50 bases in length that fold into defined secondary and tertiary structures, such as stem-loops or G-quartets. Nucleic acid aptamers preferably bind the target molecule with a $K_d$ less than $10^{-6}$, $10^{-8}$, $10^{-10}$, or $10^{-12}$. Nucleic acid aptamers can also bind the target molecule with a very high degree of specificity.

Nucleic acid aptamers are typically isolated from complex libraries of synthetic oligonucleotides by an iterative process of adsorption, recovery and re-amplification. For example, nucleic acid aptamers may be prepared using the SELEX (Systematic Evolution of Ligands by Exponential Enrichment) method. The SELEX method involves selecting an RNA molecule bound to a target molecule from an RNA pool composed of RNA molecules each having random sequence regions and primer-binding regions at both ends thereof, amplifying the recovered RNA molecule via RT-PCR, performing transcription using the obtained cDNA molecule as a template, and using the resultant as an RNA pool for the subsequent procedure. Such procedure is repeated several times to several tens of times to select RNA with a stronger ability to bind to a target molecule. The base sequence lengths of the random sequence region and the primer binding region are not particularly limited. In general, the random sequence region contains about 20 to 80 bases and the primer binding region contains about 15 to 40 bases. Specificity to a target molecule may be enhanced by prospectively mixing molecules similar to the target molecule with RNA pools and using a pool containing RNA molecules that did not bind to the molecule of interest. An RNA molecule that was obtained as a final product by such technique is used as an RNA aptamer.

Peptide aptamers are proteins that are designed to interfere with other protein interactions inside cells. They consist of a variable peptide loop attached at both ends to a scaffold. This double structural constraint greatly increases the binding affinity of the peptide aptamer to levels comparable to an antibody. The variable loop length is typically composed of about ten to twenty amino acids, and the scaffold may be any protein which has good solubility. Currently, the bacterial protein Thioredoxin-A is the most used scaffold protein, the variable loop being inserted within the reducing active site, the two Cysteines lateral chains being able to form a disulfide bridge. Peptide aptamer selection can be made using different systems, but the most used is currently the yeast two-hybrid system. Peptide aptamer can also be selected from combinatorial peptide libraries constructed by phage display and other surface display technologies such as mRNA display, ribosome display, bacterial display and yeast display. These experimental procedures are also known as biopannings. Among peptides obtained from biopannings, mimotopes can be considered as a kind of peptide aptamers. All the peptides panned from combinatorial peptide libraries have been stored in a special database with the name MimoDB.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). They can also be derived or from blood if they are genetically engineered to express antitumor T cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. US 2011/0052530 relates to a method for performing adoptive cell therapy to promote cancer regression, primarily for treatment of patients suffering from metastatic melanoma, which is incorporated by reference in its entirety for these methods.

In some embodiments, nonmyeloablative lymphodepleting chemotherapy is administered to the mammal prior to administering to the mammal the expanded tumor-infiltrating lymphocytes. The purpose of lymphodepletion is to make room for the infused lymphocytes, in particular by eliminating regulatory T cells and other non-specific T cells which compete for homeostatic cytokines. Nonmyeloablative lymphodepleting chemotherapy can be any suitable such therapy, which can be administered by any suitable route known to a person of skill. The nonmyeloablative lymphodepleting chemotherapy can comprise, for example, the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 40-80 mg/kg, such as around 60 mg/kg of cyclophosphamide is administered for approximately two days after which around 15-35 mg/m$^2$, such as around 25 mg/m$^2$ fludarabine is administered for around five days, particularly if the cancer is melanoma.

Preferably, expanded lymphocytes produced by the disclosed methods are administered as an intra-arterial or intravenous infusion, which preferably lasts about 30 to about 60 minutes. Other examples of routes of administration include intraperitoneal, intrathecal and intralymphatic. Likewise, any suitable dose of lymphocytes can be administered. In one embodiment, about $1\times10^{10}$ lymphocytes to about $15\times10^{10}$ lymphocytes are administered.

The disclosed compositions and methods can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

In order to actively drive an antitumor immune response, therapeutic cancer vaccines have been developed. Unlike the prophylactic vaccines that are used preventatively to treat infectious diseases, therapeutic vaccines are designed to treat established cancer by stimulating an immune response against a specific tumor-associated antigen. In 2010, sipuleucel-T (Provenge; Dendreon Corporation) was approved by the FDA for the treatment of metastatic, castration-resistant prostate cancer based on the results of the IMPACT (Immunotherapy Prostate Adenocarcinoma Treatment) trial in which it improved OS by 4.1 months and reduced the risk of death by 22% versus placebo. The advantage of active immunotherapies is that they have the potential to provide long-lasting anticancer activity by engaging both the innate and adaptive arms of the immune response. While mAbs are typically considered passive immunotherapies, there is increasing evidence that they also induce an adaptive immune response via a "vaccination-like" effect.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

Numerous anti-cancer drugs are available for combination with the present method and compositions. The following is a non-exhaustive lists of anti-cancer (anti-neoplastic) drugs that can be used in conjunction with irradiation: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The cancer treated by the disclosed compositions and methods can in some aspects be any solid tumor for which TILs can be produced. The cancer can also be metastatic and/or recurrent. Non-limiting examples of cancers include acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahcpatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colorectal cancer, and hepatobiliary cancer.

Triple Negative Breast Cancers (TNBCs), representing about 15% of all breast cancers, are highly aggressive type of tumors that lack estrogen receptor (ER), progesterone receptor (PR), and ERBB2 (HER2) gene amplification. TNBCs do not respond to hormonal therapy such as tamoxifen or aromatase inhibitors or therapies that target HER2 receptors, such as Herceptin (trastuzumab). Because of limited targets that are available for TNBCs, currently there is an intense interest in finding new targets and thus personalized medications that can treat this type of breast cancer. Therefore, in some embodiments, the cancer is a triple negative breast cancer (TNBC).

Definitions

The term "subject" refers to any individual who is the target of administration or treatment. The subject can be a vertebrate, for example, a mammal Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "hyperplastic cell" or "hyperplasm" refers to a cell undergoing physiological (normal) cell proliferation ("hyperplasia").

The term "neoplastic cell" or "neoplasm" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasis to other locations of the body.

The term "tumor" refers to an abnormal mass of tissue containing neoplastic cells.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The terms "peptide," "protein," and "polypeptide" are used interchangeably to refer to a natural or synthetic molecule comprising two or more amino acids linked by the carboxyl group of one amino acid to the alpha amino group of another.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "tumor infiltrating lymphocyte" or "TIL" refers to white blood cells that have left the bloodstream and migrated into a tumor.

The term "regression" does not necessarily imply 100% or complete regression. Rather, there are varying degrees of regression of which one of ordinary skill in the art recognizes as having a potential benefit or therapeutic effect. The term also encompasses delaying the onset of the disease, or a symptom or condition thereof.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Manipulating the Tumor Microenvironment Ex Vivo for Enhanced Expansion of Tumor-Infiltrating Lymphocytes for Adoptive Cell Therapy Materials and Methods Agonistic anti-4-1BB antibody. A fully-human IgG4 monoclonal agonistic anti-4-1BB antibody (mAb) (BMS 663513 Lot 6A20383/1187261) was provided by Bristol Myers Squibb at a concentration of 14.4 mg/ml and subsequently stored in aliquots at a concentration of 1 mg/ml at −80° C. The anti-4-1BB antibody was added at day 0 of the fragment set up at different concentrations and subsequently each time the TILs were fed. A more detailed description of the fragment set up is described below. 10 μg/ml was found to be the optimal dose and this concentration used for the remainder of the experiments. In addition, tumor fragments were cultured in the presence of 10 μg/ml anti-human PD-1 antibody (BMS 936558), anti-human PD-L1 antibody (cloneM1H1) (eBioscience, San Diego, Calif.), or 10 μg/ml anti-human CTLA-4 antibody (Ipilimumab, BMS) in some experiments.

Melanoma Tumor Fragment Cultures.

All studies were performed under approved Institutional Review Board (IRB) laboratory protocols at MD Anderson Cancer Center (MDACC) and H. Lee Moffitt Cancer Center. Melanoma tumors were surgically resected from stage IIIc-IV melanoma patients at MD Anderson Cancer Center and Moffitt Cancer Center as part of ongoing Phase II TIL adoptive cell therapy trials at both centers. In each case, the same protocol for tumor handling and processing were used. The tumor was cut up into 4-6 mm$^2$ fragments using a sterile scalpel and the fragments placed in wells of a 24 well plate with TIL culture media (TIL-CM) and 6,000 IU/ml Interleukin-2 (IL-2). The TIL-CM contained RPMI 1640 with Glutamax (Gibco/Tnvitrogen; Carlsbad, Calif.), 1×Pen-Strep (Gibco/Invitrogen; Carlsbad, Calif.), 50 μm 2-mercaptoethanol (Gibco/Invitrogen; Carlsbad, Calif.), 20 μg/ml Gentamicin (Gibco/Invitrogen; Carlsbad, Calif.), and 1 mM pyruvate (Gibco/Invitrogen; Carlsbad, Calif.). Each well contained 1 fragment and the fragments were kept in culture for a period of 3 weeks. For control cultures, the fragments were placed in 6,000 IU/ml IL-2 with a fully-human IgG4 Isotype control (Eureka therapeutics ET904) in some experiments. The control cultures are referred to as 'IL-2' in this Example.

Rapid Expansion of TIL.

In some cases, the TIL isolated after 3 weeks from the tumor fragment cultures were subjected to secondary expansion using a Rapid Expansion Protocol (REP). The TIL were washed in TIL-CM for 5 minutes at 1400 rpm and $1.3 \times 10^5$ cells were placed in a T25 flask with 10 ml TIL-CM and 10 ml AIM-V, 30 ng/ml anti-CD3 (OKT3) and $26 \times 10^6$ gamma-irradiated (2,500 Rads) allogeneic PBMC referred to as 'feeder cells'. On day 2 of the REP, 3,000 IU/ml IL-2 was added to the cultures and subsequently each time the TIL were fed (day 5, 7, 9, and 12) with fresh media in order to maintain the cultures between $1\text{-}2 \times 10^6$ viable cells per ml. After the 2 week expansion, the TIL were referred as 'post-REP' TIL.

Fresh Fragment Flow Cytometry Staining.

Melanoma fragments were cut up into 4-6 mm$^2$ pieces and mechanically disaggregated using glass slides, filtered, re-suspended in 2 ml sterile FACS Wash Buffer (FWB), and washed for 5 minutes at 1400 rpm. The FWB contained 1× Dulbecco's Phosphate Buffered Saline (D-PBS) and 1% Bovine Serum Albumin (BSA) (Sigma Aldrich). One week after the fragments were set up with or without the anti-4-1BB antibody, the fragment was mechanically disaggregated, filtered, and washed with FWB for 5 minutes at 1400 rpm. The cells that grew out of the fragment were also collected and re-suspended in 2 ml FWB and washed for 5 min at 1400 rpm. The cells were then stained with fluorochrome-conjugated monoclonal antibodies that recognized surface markers CD11c, CD80, CD86, 4-1BB, 4-1BBL, HLA-DR, CD3, CD8, CD56, CD19, CD20, CD4, (eBioscience, BD Biosciences, and BD Pharmingen) and AmCyan Aqua live/dead fixable dye (Molecular Probes by Life Technologies; Lot 1413034) in 0.1 ml FACS Stain Buffer (FSB) for 25 minutes on ice. The FSB contained 1×D-PBS, 1% BSA, and 5% goat serum. The cells were then washed in FWB for 5 minutes at 1400 rpm and fixed in 1×D-PBS, 1% para-formaldehyde solution. The cells were then acquired using a BD FACScanto II flow cytometer machine using FACSDiva software.

NFκB, and IκBα Staining Using Flow Cytometry in Early Cultures.

Tumors were cut up into multiple fragments, placed in TIL-CM, IL-2±anti-4-1BB antibody. After 1 week, the fragments and the cells that migrated out of the tumor fragments were harvested. The fragments were mechanically disaggregated and filtered. The fragments and the cells that migrated out of the fragment were combined, washed with FWB, and subsequently stained for cell surface markers CD3 FITC (BD Biosciences; Catalog number 555916; Lot 17763) and CD8 Pacific Blue (BD Pharmingen; Catalog number 558207; Clone RPA-T8) on ice for 25 minutes. After the surface staining was done, the cells were washed in 2 ml FWB two times. The supernatant was aspirated and 1 ml fixation buffer (BD Bioscience; Catalog 554655) was added to each tube and the tubes were placed at room temperature (RT) for 20 minutes. After 20 minutes, the cells were washed with FWB for 5 minutes at 1400 rpm, 4° C. The supernatant was aspirated and 100 µl Perm Buffer III (BD; Catalog 558050; Lot 2128930) was added to each tube while vortexing each tube. The tubes were then placed on ice for 30 minutes and washed twice in 1 ml FWB for 5 minutes, 1400 rpm, 4° C. The cells were then stained using anti-NFκB (p65) Alexa 647 (BD Pharmingen; Catalog number 560335) or anti-IκBα Alexa 647 (BD Pharmingen; Catalog number 560817) and left in the dark at RT for 1 hour. The cells were then washed with 3 ml FWB for 5 minutes, 1400 rpm, 4° C., then re-suspended in 300 µl FWB and samples were subsequently acquired using a BD FACScanto II flow cytometer machine.

Intracellular Phoshoflow-Staining of TIL.

The melanoma tumors were cut up into multiple fragments and placed in a 24-well plate with TIL-CM, IL-2±anti-4-1BB antibody. After 3 weeks, the TIL were harvested, washed twice in media for 5 minutes at 1400 rpm at 4° C. After, 250,000 TIL per well were placed in a 48-well plate and kept at 37° C. for 3-4 hours. After the 3-4 hour incubation period, 200 IU/ml IL-2 was added to the cultures. As a control, half the cultures were not given IL-2. The plate was then placed in 37° C. for 20 minutes. The flow cytometry tubes were labeled and 1 ml fixation buffer was added to each tube. The TIL were then added to the tubes, re-suspended and placed in 37° C. incubator for 10 minutes. After 10 minutes, the cells were spun for 5 minutes at 1400 rpm at 4° C. After the wash, the supernatant was aspirated and 1 ml Perm Buffer III was added to the tubes, re-suspended and placed in 4° C. for 20 minutes. The cells were then washed twice in 1 ml stain buffer for 5 minutes at 1400 rpm, 4° C. The cells were then stained with antibodies against CD8, pSTAT5, and CD3 in a total volume of 100 µl for 30 minutes at RT. After 30 minutes, the cells were washed with 3 ml stain buffer for 5 minutes, 1400 rpm at 4° C., then re-suspended with 300 µl stain buffer and the samples were acquired using a BD FACScanto II flow cytometer machine.

TIL Staining Using Flow Cytometry after 3 Weeks in Culture.

Fragments from melanoma tumors were set up as described earlier with or without the addition of agonistic anti-4-1BB antibody. After 3 weeks in culture, the TIL were harvested and stained for surface and intracellular markers using flow cytometry. Briefly, the TIL were harvested, counted, and washed with 2 ml FWB for 5 minutes at 1400 rpm. The cells were stained with surface markers CD3, CD4, CD25, CD27, CD28, and CD8 (eBiosciences, BD Pharmingen, and BD Biosciences). The viability dye AmCyan Aqua (Molecular Probes by Life Technologies) was added to gate out dead cells while acquiring the stained samples. The cells were stained in FSB for 25 minutes on ice. The cells were then washed with 2 ml FWB and BD Cytofix/Cytoperm Fixation and Permeabilization Solution (BD Biosciences Cat: 554722) (used for Granzyme B, bcl-2, and EOMES) or Perm Buffer III (BD Biosciences Cat: 558050) was used for bcl-6. The buffers were added to the samples for 20 minutes at RT in the dark. After, the cells were washed with 1X BD Perm/Wash Buffer (Cat: 554723) for 5 minutes at 1400 rpm, followed by intracellular staining for Foxp3, Granzyme B, bcl-2, EOMES, and bcl-6 (eBiosciences, BD Biosciences) in 1× Fixation Buffer for 25 minutes on ice. The samples were then washed with FWB for 5 minutes at 1400 rpm and fixed in 1×D-PBS, 1% para-formaldehyde solution. The samples were acquired using a BD FACScanto II flow cytometer machine. In some cases, harvested cells after 3 weeks of culture were stained for cell surface markers together with a MART-1 peptide HLA-A0201 tetramer (Beckman-Coulter) to enumerate the frequency of CD8$^+$ MART-1-specific T cells.

Staining for Interferon-Gamma and Degranulation (CD107a) in the TIL after 3 Week Culture Period.

Melanoma tumors were surgically resected, cut up into multiple fragments, and placed in culture with TIL media, IL-2, with or without the addition of an anti-4-1BB antibody. After 3 weeks, the TIL were set up at a 1:1 ratio with HLA-matched melanoma tumor lines in a 96-well plate for 1 hour at 37° C. After, Golgi-Stop (BD Biosciences Catalog 554724) was added to each well and the cultures were left at 37° C. for a 5 hour period. During this time, CD107a antibody (BD Biosciences) was also added to each condition. After 5 hours, the cells were harvested, washed with FWB for 5 minutes at 4° C. The cells were then stained for surface markers CD3 and CD8 for 25 minutes at 4° C. After, the cells were washed with FWB again, re-suspended in fixation buffer (added while vortexing the tubes) and incubated for 15 minutes at room temperature. After, the cells were washed with FWB and re-suspended in Cytofix/Cytoperm buffer and incubated at room temperature for 20 minutes. The cells were then washed with FWB and stained for IFN-gamma for 25 minutes in 4° C. The cells were then washed again and the samples were acquired using a BD FACScanto 11 flow cytometer machine.

Cytospin and immunocytochemistry staining for surface and nuclear markers.

The tumor fragments were set up as previously described with or without anti-4-1BB antibody. After 1 week in culture, the cells were collected and washed twice in 1×D-PBS for 5 minutes at 1400 rpm. The cells were re-suspended in 1 ml 4% para-formaldehyde for 20 minutes at RT. The cells were washed again in 1×D-PBS and re-suspend in 1 ml and placed at 4° C. The washed cells were cytospun onto glass slides at 750 rpm for 3 minutes using Shandon Cytospin II centrifuge. The samples for Ki67 (Dako) and NFκB (p65) (BD transduction laboratories) (nuclear staining) were placed in PBS, 0.2% Triton X-100 solution for 10 min at RT and washed in 1×D-PBS 3 times. All samples were then placed in 3% $H_2O_2$/methanol for 10 minutes at RT to block endogenic peroxidase. The samples were then washed 3 times in 1×D-PBS and 2.5% normal horse serum (Vectastain Universal Elite ABC Kit) was added to all slides for 30 minutes in a humid chamber at RT followed by addition of the primary antibody at 4° C. overnight. The next day, a biotinylated secondary antibody was added to the samples for 30 min at RT (Vectastain Universal Elite ABC Kit). The slides were then washed 3 times in D-PBS and peroxidase-conjugated avidin biotin complex ABC Reagent (Vectastain Universal Elite ABC Kit) was added for 30 min at RT. The samples were then washed with D-PBS and 3,3-Diaminobenzidine (DAB) was added. The samples were then counterstained and covered. Analysis was done using Leica Application Suite (LAS) V4.2 software (Leica Microsystems). For NFκB (p65) staining, analysis was also done using the LAS V4.2 software, but additional analysis was conducted using Vectra Intelligent Slide Analysis System (Vectra, Perkin Elmer) Nuance software 3.0.1.2, using composite coloring style "Fluorescence."

Blocking MHC/HLA Class I in Fragment Cultures.

The melanoma tumor was surgically resected and cut up into multiple fragments. The fragments were then placed in culture with an anti-HLA-ABC blocking antibody (anti-HLA antibody) at a concentration of 80 µg/ml for 3 hours at 37° C. IL-2 alone or IL-2 plus anti-4-1BB antibody (10 µg/ml) was then added. The cultures were subsequently fed with additional anti-MHC antibody once more and all cultures were fed over a 3 week period with media, IL-2±anti-4-1BB antibody. The viable cells after 3 weeks were counted and stained for CD3 and CD8 using flow cytometry.

Measurement of Anti-Tumor Reactivity of TIL Using IFN-Gamma ELISA.

After 3 weeks of tumor fragment culture, the TIL were isolated, washed and co-cultured overnight in round-bottom 96-well plates at a 1:1 ratio with tumor target cells from autologous or HLA-A-matched melanoma tumor cell lines ($1\times10^5$ TIL and $1\times10^5$ tumor targets). Tumor target cells from HLA-A unmatched tumor cell lines were used as negative controls for specificity. Triplicate wells were set up for each condition. The supernatants were collected after 24 hr and IFN-gamma secretion was measured using a human IFN-gamma ELISA kit (Thermo Scientific KB132422). A 96-well ELISA plate reader (ELx808, Bio-Tek Instruments Inc., Houston, Tex.) was used to read the plate.

Murine TIL.

Six to eight week-old C57BL/6 mice were purchased from Harlan Laboratories Indianapolis, Ind.) and were housed at the Animal Research Facility of the H. Lee Moffitt Cancer Center and Research Institute. All animal protocols were reviewed and approved by the Institutional Animal Care and Use Committee at the University of South Florida. B16 melanoma cancer cells were maintained by serial in vitro passages in complete medium (CM) consisting of RPMI 1640 supplemented with 10% heat-inactivated FCS, 0.1 mM non-essential amino acids, 1 mM sodium pyruvate, 2 mM fresh L-glutamine, 100 µg/ml streptomycin, 100 U/mL penicillin, 50 µg/ml gentamycin, 0.5 µg/mL fungizone (all from Life Technologies, Rockville, Md.), and 0.05 mM 2-ME (Sigma-Aldrich, St. Louis, Mo.). A total of $1\times10^5$ B16 cells were injected subcutaneously (s.c.). In some experiments, mice received 20 mg/kg of rat IgG (rIgG) or anti-mouse PD-1 antibodies (clone RMP1-14, BioXcell, West Lebanon, N.H.) intraperitoneally (i.p.) every 3 days. Tumors were collected on days 21-24. Tumor cell suspensions were prepared from solid tumors by enzymatic digestion in HBSS (Life Technologies) containing 1 mg/ml collagenase, 0.1 mg/ml DNAse I, and 2.5 U/ml of hyaluronidase (all from Sigma-Aldrich) with constant stirring for 2 hours at RT. The resulting suspension was passed through a 70-µm cell strainer and labeled with anti-CD90 microbeads according to the manufacturers' instructions (Miltenyi Biotec) and purified using an autoMACS. Purified TIL were cultured for 7 days in the presence of 6000 IU/ml IL-2 alone or in combination with 10 µg/ml non-specific control IgG or anti-mouse 4-1BB antibodies (clone 3H3, BioXcell). On day 7, TIL were collected and co-cultured with MC-38 or B16 cells at a 10:1 ratio. After 24 hours, supernatants were collected and IFN-gamma secretion was measured by ELISA.

Statistical Analysis.

Statistical analysis for comparison of the 2 groups was done using the student T-test or the Wilcoxon signed rank test (paired datasets). Analysis of experiments with 3 or more treatment groups was done using the one-way or two-way analysis of variance (ANOVA), with Tukey post-tests with both tests using biological relevance occurring when $p<0.05$. Statistical analysis was done using Graph Pad Prism (La Jolla, Calif.).

Results 4-1BB is Expressed on Freshly Isolated Melanoma Tumor-Infiltrating Lymphocytes and after 1 Week of Tumor Fragment Culture.

Some $CD3^+CD8^+$ TIL expanded from tumor fragments expressed 4-1BB [Hernandez-Chacon, J A, et al (2011) J Immunother 34(3):236-50], so experiments were conducted to determine whether 4-1BB was expressed on the freshly isolated TIL from melanoma tumors used to derive tumor fragment cultures. Melanoma tumors were surgically resected from metastatic melanoma patients and single cell suspensions were prepared and stained for 4-1BB on the $CD3^+CD8^+$ subset. In 18 independent freshly isolated TIL samples, 4-1BB was mainly expressed on $CD8^+$ TIL, whereas OX40 was also expressed but to a lesser extent (FIG. 1A). The expression of 4-1BB and OX40 was also examined on $CD3^+CD8^+$ subset after the TIL were in culture for 1 week (FIG. 1B). Some TIL still expressed 4-1BB even after 1 week of culture, whereas OX40 was also expressed but at lower levels as expected on $CD8^+$ T cells (FIG. 1B). Thus, 4-1BB is expressed on $CD8^+$ T cells in tumor tissue ex vivo with a population of $4-1BB^+$ cells still detectable after a week of culturing the tumor fragments.

Agonistic Anti-4-1BB Antibody Increases TIL Expansion In Vitro.

The detection of $4-1BB^+$ $CD8^+$ T cells in the isolated tumor fragments prompted the question whether co-stimulation of 4-1BB in these early cultures could affect the outcome of TIL outgrowth. A co-stimulatory anti-4-1BB antibody from Bristol Myers Squibb (BMS) was tested [Hernandez-Chacon, J A, et al (2011) J Immunother 34(3): 236-50; Chacon, J A, et al (2013) PLoS One 8(4):e60031]. Melanoma tumors were surgically resected from patients and cut into four 3-5 $mm^2$ fragments per condition and cultured in a 24 well plate over a 3 week period. Dose titration experiments were conducted with the anti-4-1BB added on day 0 of culture to determine the optimal concentration of antibody that would increase the yield of $CD8^+$ T cells from the fragments (FIG. 8). As shown in FIG. 8A, 10 µg/ml anti-4-1BB antibody produced the most consistent result in terms of enhancing total TIL and $CD8^+$ TIL outgrowth. Although higher concentration of anti-4-1BB may have been active even more, this 10 µg/ml dose was used in subsequent experiments to minimize antibody usage and prevent the possibility of over-dosing with too much 4-1BB co-stimulation. In subsequent experiments this 10 μg/ml dose was used each time the TIL were fed or sub-cultured with fresh media and IL-2.

Experiments were conducted to test how addition of anti-4-1BB affects total TIL yield and the rate of TIL outgrowth from the tumor fragments in a larger number of patient tumor samples. Addition of 4-1BB markedly accelerated the rate of TIL outgrowth over the first two weeks of culture in 1 representative patient tumor samples or 4 independent tumor fragments (FIG. 2A). This was associated with a marked increase in proliferating cells emanating from the fragments during the first 7 days in culture, as shown by the increased nuclear Ki67 staining of isolated cells surrounding the tumor fragments after cytospin (FIG. 2B; four independent experiments). To further test the effects of anti-4-1BB, experiments were performed on an additional seven tumor samples (28 separate tumor fragments), which revealed this enhanced outgrowth of TIL after 3 weeks from a consistent phenomenon in a larger sampling of patient tumors (FIG. 2D). Experiments were then conducted to determine how anti-4-1BB facilitates TIL outgrowth compared to three other immunomodulatory (checkpoint) antibodies, anti-PD-1, anti-PD-L1, and anti-CTLA-4 at the same dose, currently being used in clinical trials and standard of care for melanoma (anti-CTLA-4). As shown in FIG. 2D, anti-4-1BB antibody was superior in inducing TIL outgrowth from the tumor fragments compared to IL-2 alone or IL-2 plus these other checkpoint antibodies.

Addition of Anti-4-1BB to Initial Tumor Fragments Pathway Activated NFκB and Increases NFκB Nuclear Translocation in TIL.

Figure 3B:
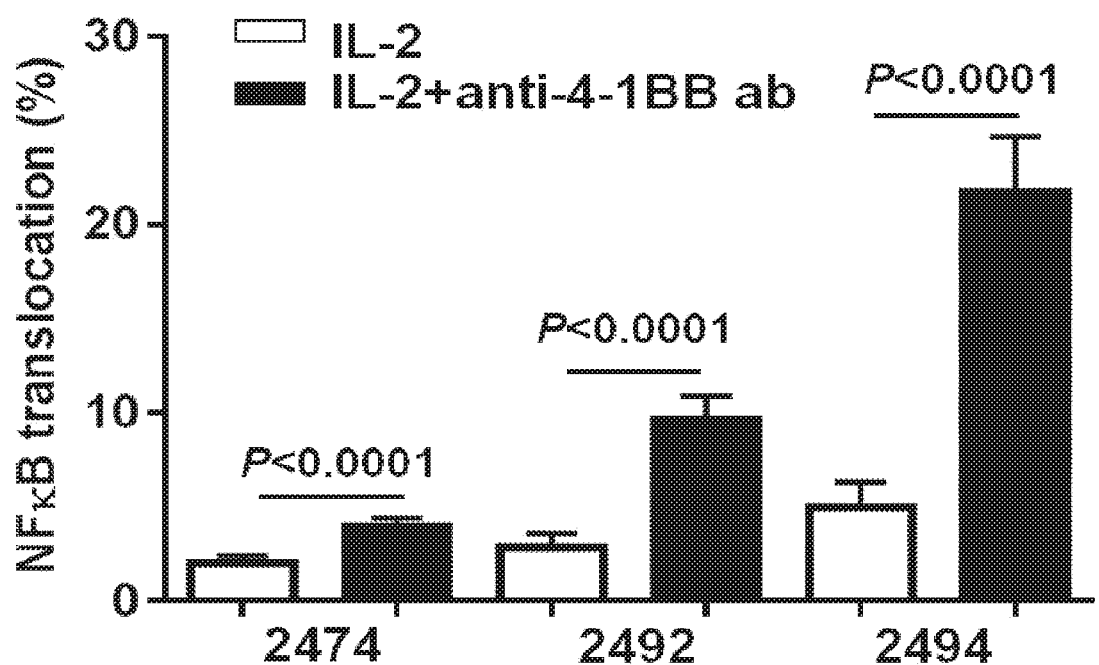

Before proceeding to determine how the outgrowth and function of $CD8^+$ T cells was affected by agonist anti-4-1BB, experiments were conducted to determine whether addition of the antibody at the start of the tumor fragment cultures induced 4-1BB co-stimulation in the TIL within the tumor microenvironment of the fragments as well as in TIL that had migrated out from the fragments. One of the key signaling pathways activated by 4-1BB co-stimulation is the activation of the classical NFκB (p65/cREL) transcription factor pathway and its translocation to the nucleus through degradation of IκBα mediated by IKKαβ complexes activated after TRAF recruitment to the 4-1BB [Kim, J O, et al (2003) FEBS Lett 541(1-3):163-70]. Melanoma tumor fragments (4 fragments per condition for each patient) were established in culture with or without addition of 10 μg/ml anti-41BB. After 1 week, the TIL that had migrated out of the tumor fragment supernatant were collected, cytospun onto glass slides, fixed and stained for NFκB (p65). The TILs grown with IL-2 and the anti-4-1BB antibody had markedly more NFκB translocation in the nucleus as compared to the TILs grown in IL-2 using a pseudo-immunofluorescence imaging system that detected NFκB (green) in the nucleus (red) (FIG. 3A). Staining for NFκB in TILs from 3 different patient tumor samples found a consistent increase in translocated p65 in cultures treated with anti-4-1BB, after quantifying the staining using this pseudo-immunofluorescent imaging approach (FIG. 3B). To look more closely inside the tumor tissue microenvironment itself, fragments were isolated 1 week after culture initiation and stained for NFκB (p65) and IκBα in the TILs using flow cytometry after the isolated fragments were mechanically disaggregated into single cell suspensions using frosted glass. After gating on viable $CD3^+CD8^+$ T cells, an increase in NFκB (p65) staining (FIG. 3C) was detected together with a marked decrease in IκBα expression, indicative of NFκB activation (FIG. 3D), in the anti-4-1BB antibody group compared to the IL-2 alone control group. These results indicate that addition of agonist anti-4-1BB antibody to melanoma tumor fragments can activate NFκB both in the T cells inside the tumor fragments as well as in those isolated outside the tumor fragments.

Activating the 4-1BB Pathway Increases the $CD8^+$ TIL Expansion.

Figure 4D:
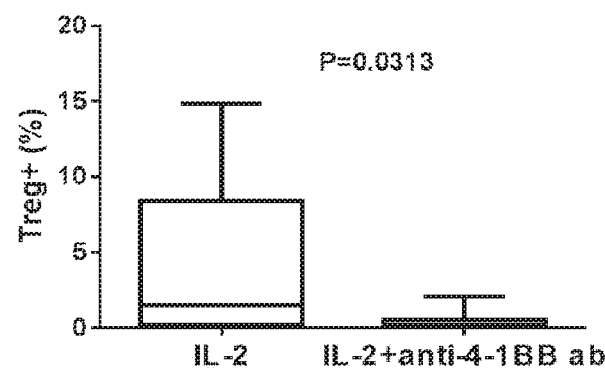

Experiments were conducted to determine whether the cells that were growing out of the fragment were enriched for $CD8^+$ T cells and also look at the yield of $CD4^+$ T cells and $CD4^+Foxp3^+$ T-regulatory cells (Tregs). Melanoma fragments from tumors from a number of patients were set up as before with or without the addition of 10 μg/ml anti-4-1BB antibody. CD8 staining of cytospun cells that were isolated from outside the tumor fragments in early cultures (after 1 week) was performed. As shown in the example staining experiment from a representative patient sample, 4-1BB co-stimulation significantly increased the number of CD8-stained cells versus IL-2 alone (FIG. 4A). Experiments were then performed using 14 patient tumor samples (representing 56 independent tumor fragments), revealing that addition of anti-4-1BB significantly increased the percentage of $CD8^+$ T cells expanded from the tumor fragments after 3 weeks (FIG. 4B), while the percentage of $CD4^+$ T cells decreased (FIG. 4C). Staining for Tregs after 3 weeks in experiments on 7 patients (28 tumor fragments) found that 4-1BB co-stimulation in these early fragment cultures reduced the frequency (FIG. 4D) and yield of Tregs.

Modulation of Melanoma TIL Effector Phenotype and Function by Activating the 4-1BB Pathway Early in Tumor Fragments.

Figure 5A:
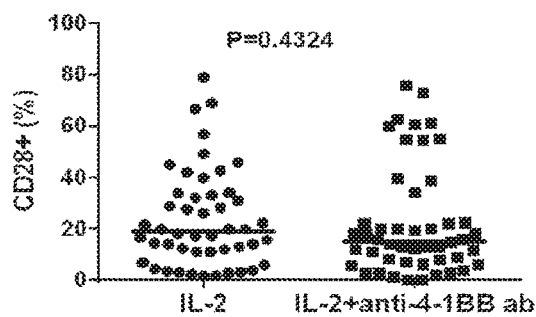
FIGS. 5A to 5G show phenotypic characterization of effector-memory markers in TIL isolated from tumor fragment cultures treated with or without-anti-4-1BB. Fragments from melanoma tumors were set up in a 24 well plate with or without anti-4-1BB antibody. 3 weeks after the initial set-up, the TILs were harvested and flow cytometry was done to analyze effector-memory markers and cytolytic granule markers. When the expression of CD28 was measured in the $CD3^+$ $CD8^+$ subset in 48 independent TIL lines, no statistical significance was found in the expression of CD28 in the $CD3^+$ $CD8^+$ subset in the different conditions (FIG. 5A). When the expression of CD27 was measured in the $CD3^+$ CD8+ population in 48 independent TIL lines, the CD27 expression in the $CD3^+$ $CD8^+$ subset was down-regulated in the TIL expanded with the anti-4-1BB antibody as compared to the TIL grown with IL-2 alone (FIG. 5B). When the expression of the cytolytic granule marker Granzyme B was measured in the $CD3^+$ $CD8^+$ subset in 48 independent TIL lines, the expression of Granzyme B was increased in the TIL expanded with IL-2 and anti-4-1BB antibody as compared to TIL expanded with IL-2 alone (FIG. 5C). When the expression of Eomes was measured using flow cytometry in 19 independent TIL, the TIL expanded with the anti-4-1BB antibody exhibited increased Eomes expression in the $CD3^+$ $CD8^+$ subset (FIG. 5D). When the percentage and mean fluorescence intensity (MFI) of the anti-apoptotic molecule, bcl-2, was determined in 13 independent TIL, the TIL expanded with the anti-4-1BB antibody exhibited an increased bcl-2 percentage and MFI (FIG. 5E). The expression of bcl-6 (FIG. 5F) in 8 independent TIL lines, and the expression of pSTAT5 was also determined in 13 independent TIL in the $CD3^+$ $CD8^+$ subset (FIG. 5G). Bcl-6 and pSTAT5 percentage and MFI was increased when the TIL were expanded with IL-2 plus anti-4-1BB antibody for 3 weeks (FIGS. 5F and 5G).
Figure 5B:
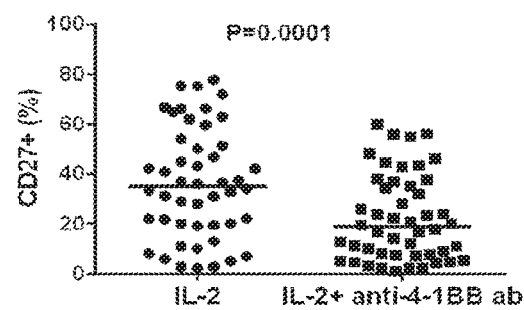

The phenotype of the $CD8^+$ TIL expanded from tumor fragments in the presence of anti-4-1BB was characterized further. Melanoma tumor fragments were cultured as before with or without anti-4-1BB antibody. After 3 weeks, the TIL were stained using flow cytometry for effector-memory markers (CD28 and CD27), markers of effector CTL (Granzyme B and Eomesodermin), and T-cell survival/memory markers (bcl-2 and bcl-6) [Huang, J, et al (2006) J Immunol 176(12):7726-35; Powell, D J, et al (2005) Blood 105(1):241-50; Ichii, H, et al (2004) J Immunol 173(2):883-91; Ichii, H, et al (2002) Nat Immunol 3(6):558-63; Pearce, E L, et al (2003) Science 302(5647):1041-3; Li, G, et al (2013) PLoS One 8(6):e67401]. In 48 independent tumor fragment lines, CD28 expression was unaltered (FIG. 5A), but CD27 expression decreased somewhat (FIG. 5B). This was associated with an increase in CD70 expression (ligand for CD27) on the harvested $CD8^+$ TIL. BTLA, another marker on $CD8^+$ TIL associated with clinical response to TIL therapy in melanoma patients [Radvanyi, L G, et al (2012) Clin Cancer Res 18(24):6758-70], was also unaltered. Other T-cell negative co-stimulatory molecules, such as PD-1 were also unaltered. Experiments were also conducted to test whether TILs that grew out of tumor fragments over the 3-week period with anti-4-1BB co-stimulation could further expand after re-stimulation through the T-Cell Receptor (TCR) in a REP. In 6 separate patient tumor samples, 4-1BB co-stimulation during the initial TIL outgrowth did not affect the fold-expansion of TIL after TCR re-stimulation in the REP (FIG. 9A) and did not alter the phenotype of the resulting post-REP cells in terms of CD8, CD28, and CD27 expression, although there was a trend towards an increased frequency of $CD8^+$ T cells (FIG. 9B-E).

Figure 5C:
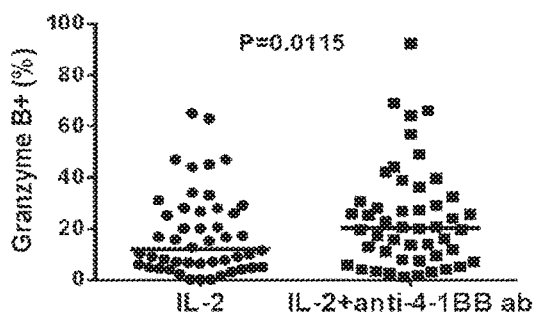
Figure 5D:
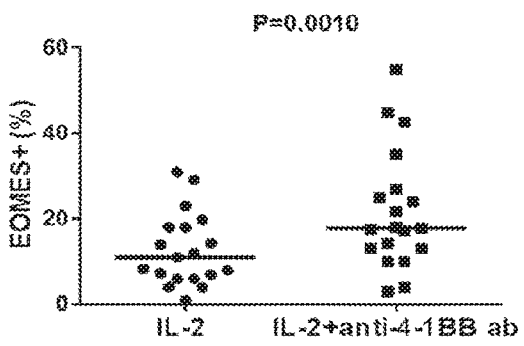
Figure 5E:
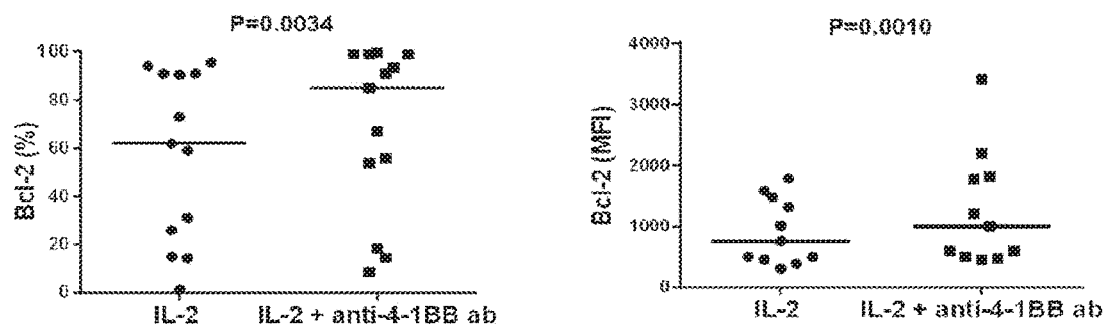
Figure 5F:
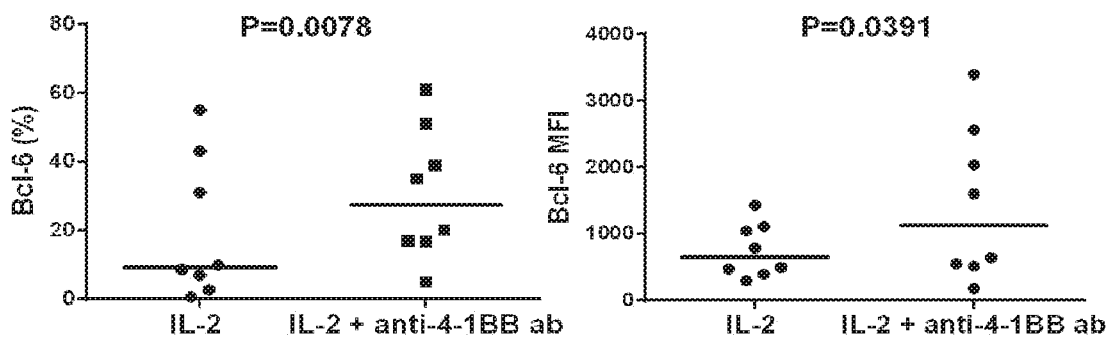

Further experiments were conducted to determine how addition of anti-4-1BB to the tumor fragments affected the expression of molecules associated with effector (Granzyme B and Eomes), memory (bcl-6 and Eomes), and survival (bcl-2 and bcl-6) functions of CTL. Intracellular staining coupled with cell surface staining for CD8 was used to measure both percentage and fluorescence intensity of these markers by flow cytometry. Granzyme B is a key cytolytic granule molecule in $CD8^+$ T cells, while Eomes is a T-box transcription factors helping drive Granzyme B expression as well as being involved in memory T-cell maintenance [Ichii, H, et al (2004) J Immunol 173(2):883-91; Ichii, H, et al (2002) Nat Immunol 3(6):558-63; Pearce, E L, et al (2003) Science 302(5647):1041-3]. Both bcl-2 and bcl-6 are cell survival (anti-apoptotic) molecules in memory T cells, with bcl-6 being also key transcription factor in the maintenance of memory status that inhibits Blimp-1 expression and terminal $CD8^+$ T-cell differentiation [Ichii, H, et al (2004) J Immunol 173(2):883-91; Ichii, H, et al (2002) Nat Immunol 3(6):558-63; Yoshida, K, et al (2006) Eur J Immunol 36(12):3146-56; Scheeren, F A, et al (2005) Nat Immunol 6(3): 303-13]. An increased intracellular expression of the Granzyme B (FIG. 5C) and Eomes (FIG. 5D) was found in $CD8^+$ TILs expanded from fragments with 4-1BB co-stimulation. In addition, both the percentage and mean fluorescence intensity (MFI) of bcl-2 and bcl-6 was increased (FIGS. 5E and F).

Figure 5G:
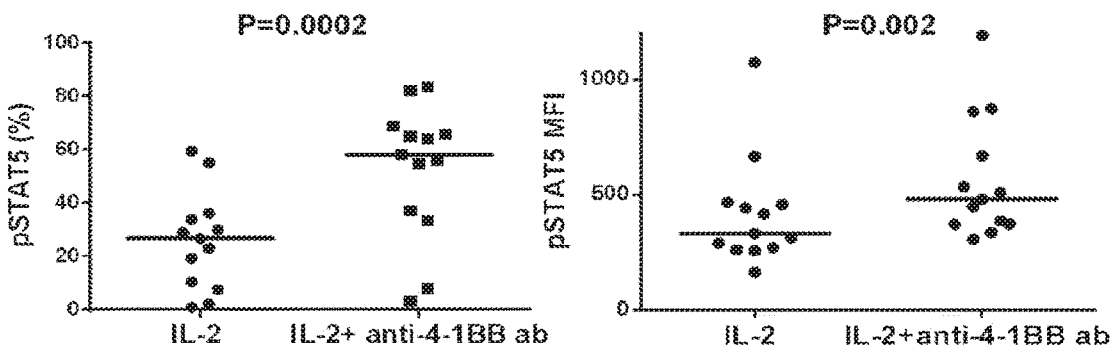

Due to the accelerated outgrowth of $CD8^+$ T cells from the tumor fragments when anti-4-1BB was added, IL-2 signaling could have been altered. Intracellular staining for tyrosine-phosphorylated STAT5 (pSTAT5) isolation of TIL after 3 weeks expansion from tumor fragment culture (13 patients) found a significantly higher frequency pSTAT5 expression as well as MFI in $CD8^+$ TIL in the anti-4-1BB treatment group (FIG. 5G).

Increased Anti-Tumor Reactivity in TIL Expanded with Anti-4-1BB Antibody.

Figure 6A:
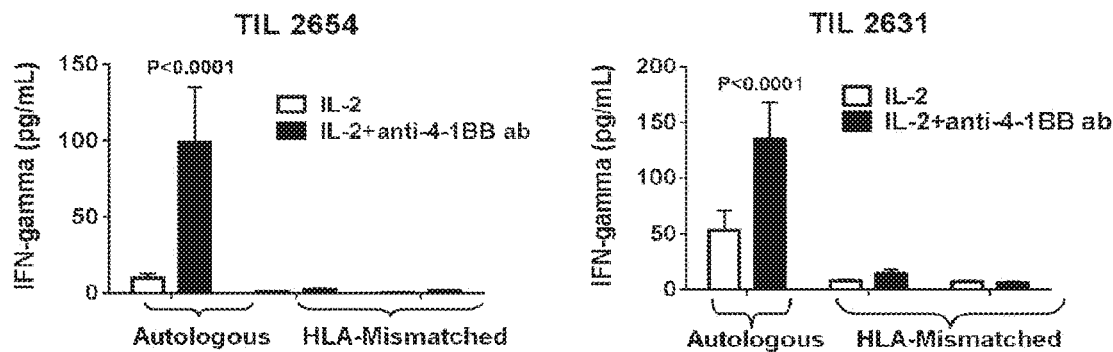
FIGS. 6A to 6E show increased tumor specificity of TIL from tumor fragment cultures treated with anti-4-1BB. After the fragments were set up with IL-2 alone or IL-2 plus anti-4-1BB antibody and expanded over a 3 week period (pre-REP), the TIL were harvested and set up at a 1:1 ratio with autologous (FIG. 6A, left and middle) or HLA-A matched (FIG. 6A, right) tumor cells. Supernatants were collected after 24 hours and IFN-gamma secretion was measured. These experiments demonstrated in 3 independent pre-REP TIL that IFN-gamma secretion was increased in the pre-REP TIL expanded with IL-2 and anti-4-1BB compared to TIL expanded with IL-2 alone (FIG. 6A). After 3 week in culture with or without the anti-4-1BB antibody, the TIL were set up at a 1:1 ratio with HLA-A matched tumor lines. Using flow cytometry, the amount of IFN-gamma+ cells was measured in the $CD3^+$ $CD8^+$ subset (FIG. 6B). In 11 independent TIL lines, the TIL expanded with anti-4-1BB antibody exhibited an increase in IFN-gamma$^+$ cells (FIG. 6B). In addition, flow cytometry was used to determine the amount of degranulation after setting up the TIL at a 1:1 ratio with HLA-A matched tumor lines (FIG. 6C). In 6 independent TIL, the TIL grown with the anti-4-1BB antibody exhibited an increase in $CD107a^+$ cells in the $CD3^+$ $CD8^+$ subset (FIG. 6C). Using flow cytometry, the percentage of MART-1$^+$ specific T cells was measured on the $CD3^+$ $CD8^+$ TIL initially expanded with IL-2 alone or IL-2 with anti-4-1BB antibody. The TIL expanded with the anti-4-1BB antibody exhibited an increase in antigen specific population, compared to the TIL expanded with IL-2 alone (FIG. 6D). The pre-REP TILs that were initially expanded with or without the anti-4-1BB antibody then underwent the secondary expansion (REP). After the 2 week expansion, the post-REP TIL were harvested and set up at a 1:1 ratio with the autologous tumor (FIG. 6E, left) or HLA-matched (FIG. 6E, middle and right) tumor cells. 24 hours later, the supernatants were collected and IFN-gamma secretion was measured using ELISA. The post-REP TIL that were initially expanded with anti-4-1BB antibody exhibited an increase in Interferon-gamma secretion compared to the TIL initially expanded with IL-2 alone (FIG. 6E).
Figure 6B:
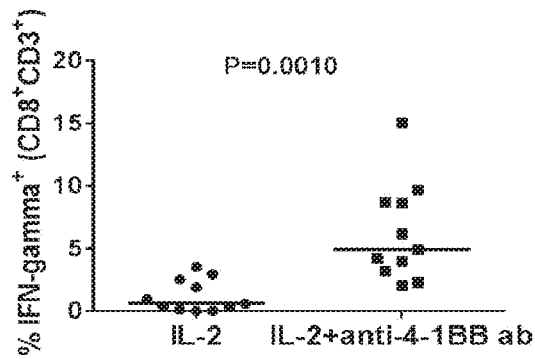
Figure 6C:
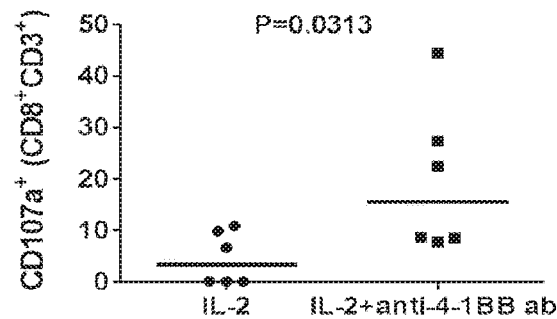
Figure 6D:
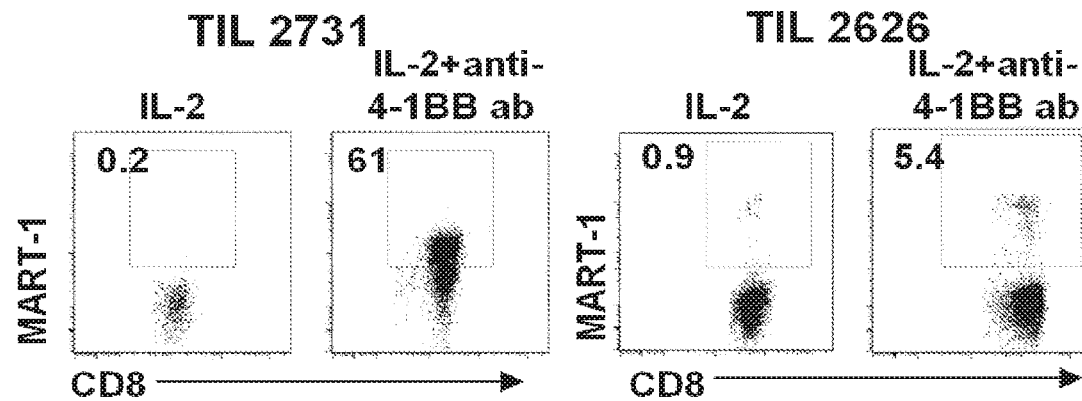
Figure 6E:
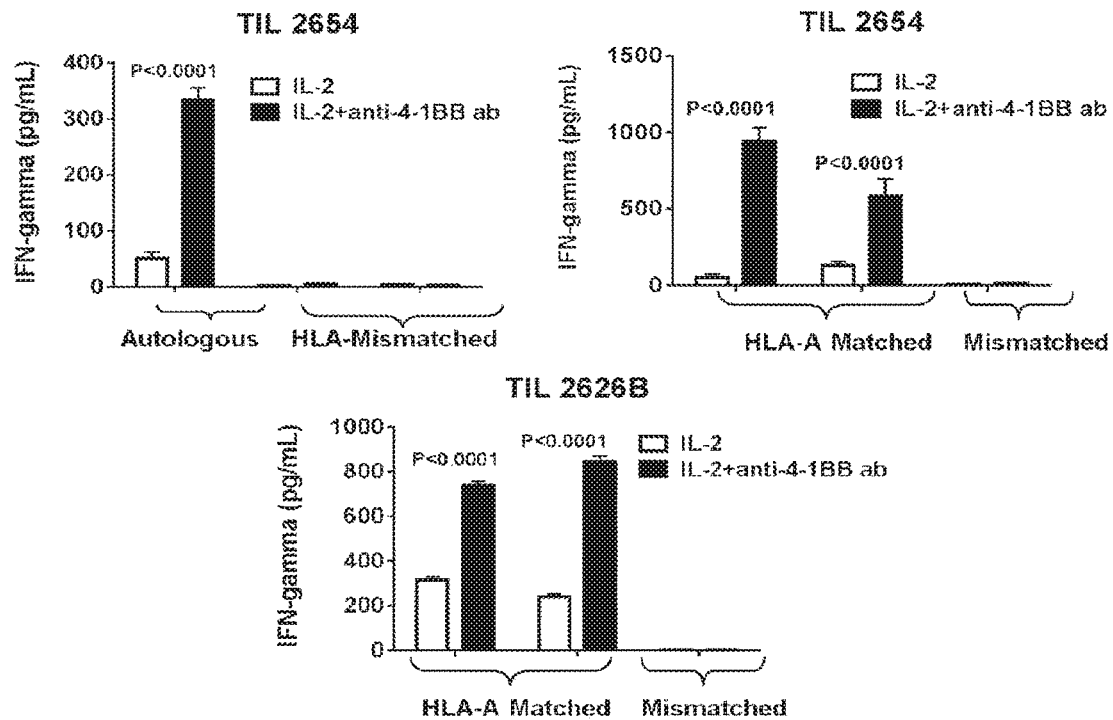

The induced expression of 4-1BB known to occur on antigen-activated $CD8^+$ T cells together with the disclosed detection of a significant frequency of $4\text{-}1BB^+ CD8^+$ TTL within tumors and during early tumor fragment culture (FIG. 1), suggests that in addition to enhancing the numerical expansion of $CD8^+$ TIL through 4-1BB co-stimulation, addition of agonist anti-4-1BB may also increase the tumor reactivity of the TIL grown out from the treated fragments. This question was tested in different ways. First, the anti-tumor reactivity of bulk TIL cultures grown out from tumor fragments after 3 weeks against autologous or HLA-A-matched allogeneic tumor lines were analyzed by measuring the extent tumor-specific IFN-gamma release after a 24-hour tumor cell-TIL co-culture assay. Provision of 4-1BB co-stimulation to the tumor fragments yielded TIL with markedly higher anti-tumor reactivity after 3 weeks of culture (FIG. 6A; data from three independent experiments shown). Second, ICS assays were performed for IFN-gamma production on a single cell level using flow cytometry of TIL isolated after 3 weeks from fragment cultures from $HLA\text{-}A2^+$ patients using $HLA\text{-}A2^+$ melanoma tumor targets, revealing a significant increase in the frequency in IFN-gamma-positive $CD8^+$ T cells in TIL isolated from fragment cultures treated with anti-4-1BB antibody (FIG. 6B; data from 11 experiments shown). The frequency of CD107a release (a measure for target-specific T-cell degranulation) was also measured using flow cytometry. TIL expanded with IL-2 plus anti-4-1BB versus IL-2 alone exhibited an increase in $CD107a^+$ frequency after co-incubation with HLA-A-matched tumor targets in the $CD3^+CD8^+$ subset (FIG. 6C; data from 6 patients). In addition, in some $HLA\text{-}A2^+$ patients, TIL that grew out from the fragments for CD8 and MART-1-specific TCR expression was stained using MART-1 peptide tetramers, revealing a marked increase in the frequency of MART-1-specific T cells when anti-4-1BB was added to the tumor fragment cultures (FIG. 6D). Finally, TILs originally expanded from tumor fragments with or without added anti-4-1BB after secondary rapid expansion (REP) using anti-CD3 plus IL-2 were analyzed for tumor-specific reactivity. Here too, an enhanced anti-tumor reactivity of the post-REP product was found when 4-1BB co-stimulation was provided in the initial tumor fragment cultures (FIG. 6E). Thus, provision of agonist anti-4-1BB antibodies to the initial melanoma tumor fragment cultures significantly increases the outgrowth of tumor-specific $CD8^+$ T cells for adoptive cell therapy.

To further investigate the ability of 4-1BB co-stimulation ex vivo to enhance TIL anti-tumor reactivity, a C57BL/6 mouse B16 melanoma tumor model was performed. Here, mice were challenged with subcutaneous B16 melanoma, the tumors isolated, and the isolated cells cultured with IL-2 with or without an agonist anti-mouse 4-1BB antibody (clone 3H3) for seven days. TILs grown with the anti-4-1BB antibody exhibited increased the anti-tumor reactivity of the expanded TILs, as determined using IFN-gamma-release after co-culture with B16 tumor targets (FIG. 10A). PD-1 blockade has been shown to facilitate anti-tumor T-cell priming, increase T-cell infiltration into tumors and anti-tumor effector function [Peng, W, et al (2012) Cancer Res 72(20):5209-18; Pilon-Thomas, S, et al (2010) J Immunol 184(7): 3442-9]. Clinical trials in melanoma have shown increased T-cell infiltration into tumors with an impressive 30% clinical response rate [Topalian, S L, et al (2014) J Clin Oncol 32:1020-1030]. The effects of prior PD-1 blockade in vivo were next determined on the expansion of tumor-specific TIL from B16 melanomas. C57BL/6 mice bearing B16 tumors were treated via intraperitoneal injection with 20 mg/kg non-specific or normal IgG (NrIgG) or blocking anti-PD-1 antibodies. Tumors were collected on day 21 and the isolated TIL were cultured in vitro in NrIgG or anti-4-1BB antibodies for seven days. Addition of anti-41BB antibodies to the in vitro culture without prior anti-PD-1 in vivo led to enhanced anti-tumor activity of the cultured T cells (FIG. 10B). However, this increased anti-tumor activity of the short-term cultured B16 TIL with anti-4-1BB was enhanced even more when mice were treated with anti-PD-1 in vivo prior to isolation of the tumors and culture of the TIL ex vivo (FIG. 10B). Thus, PD-1 blockade in vivo prior to TIL expansion from resected tumors improves the effects of agonist anti-4-1BB antibody in enhancing anti-tumor reactivity of expanded TIL.

Anti-4-1BB Addition Modulates the Phenotype of Resident Dendritic Cells in Melanoma Tumor Fragments.

Figure 7A:
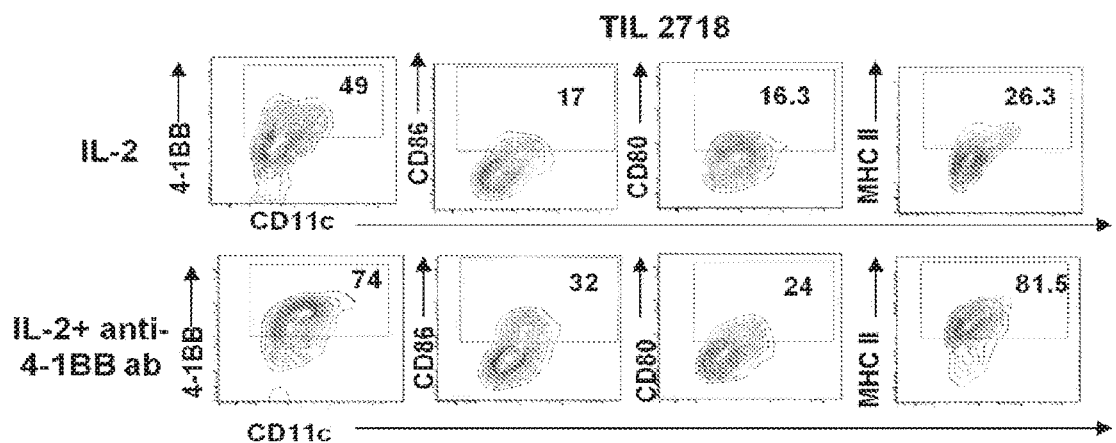
FIGS. 7A to 7E show that addition of anti-4-1BB antibody to the melanoma fragments increased dendritic cell activation markers and addition of anti-MHC-I antibody decreases expansion of $CD8^+$ TIL. The melanoma tumors were cut up into multiple fragments and placed in culture with IL-2 alone or IL-2 anti-4-1BB antibody. After 1 week in culture, the fragments were mechanically disaggregated, filtered, and stained for DC and their activation markers. In 1 representative TIL sample, the DC expressed 4-1BB and the addition of the anti-4-1BB antibody increased CD86, CD80 and MHC II expression (FIG. 7A). When live, $CD3^-CD11c^+$ cells were examined, the DC had a more activated phenotype with increased MHC-II (FIG. 7B), CD86 (FIG. 7C) and CD80 (FIG. 7D) when anti-4-1BB antibody was added compared to the cultures grown in IL-2 alone. This was demonstrated in 8 independent TIL samples for MHC II (FIG. 7B), 7 independent TIL for CD86 expression (FIG. 7C), and 6 independent TIL for CD80 expression (FIG. 7D). The melanoma fragments were set up with or without the addition of an anti-MHC-I (anti-HLA-ABC) antibody. After 3 hours, IL-2±anti-4-1BB antibody was added to the cultures. After 3 weeks, the cells were stained using flow cytometry and viable cell counts were conducted. When MHC-I was blocked, there was a decrease in the expansion of $CD8^+$ TIL (FIG. 7E) as demonstrated in 2 independent TIL lines.
Figure 7B:
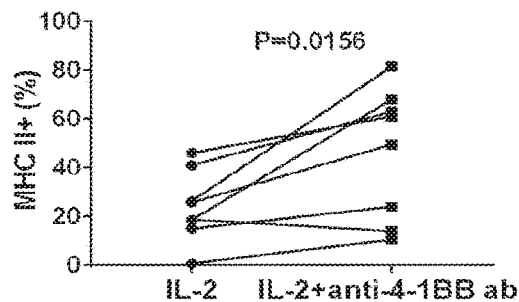
Figure 7C:
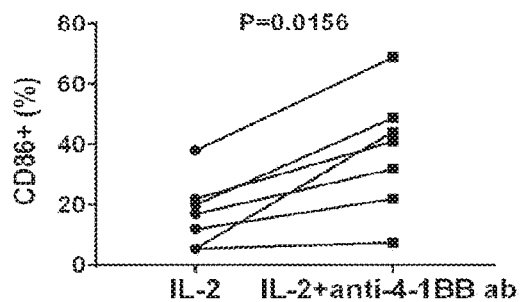
Figure 7D:
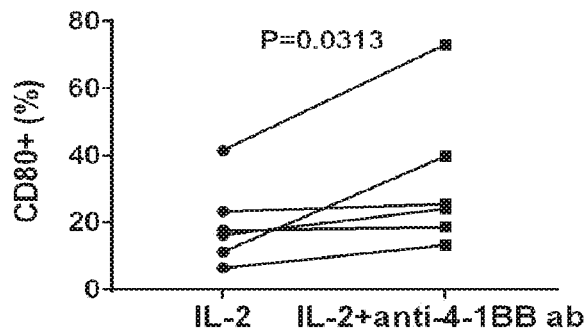

The observation that agonist anti-4-1BB antibodies activate $CD8^+$ T cells in the tumor microenvironment within the tumor fragments, as indicated by the activation of NFκB and increased Ki67 expression, suggested that other tumor-resident leukocyte populations may also be affected by 4-1BB co-stimulation given in this context. Flow cytometry analysis of cell suspensions obtained from tumor fragments that were in culture for 7 days was first performed to determine what other viable (surviving) resident cells were present and expressing 4-1BB that may be targeted by the added antibody. Staining was done for dendritic cells (DC), T cells, NK cells, and B cells. Very few NK cells ($CD3^- CD56^+$) and B cells ($CD3^- CD20^+$) were found in the tumor fragments and these had no detectable 4-1BB expression. $CD8^+$ and $CD4^+$ T cells ($CD3^+CD8^+$ and $CD3^+CD4^+$, respectively) were detected, with only the $CD8^+$ cells expressing detectable 4-1BB. Interestingly, when staining was done for DC (CD3$^-$CD11c$^+$HLA class II$^+$), a considerable frequency of viable 4-1BB$^+$ DC were found persisting in these fragments (FIG. 7A; left side contour plots) and, moreover, addition of the agonist anti-4-1BB during the tumor fragment culture set-up seemed to activate these DC, as found by a marked increase in CD86 and HLA class II expression in the gated live CD3$^-$CD11c$^+$ subset in a representative set of fragments (FIG. 7A). This was examined in tumor fragment cultures from resected melanomas from 8 patients, revealing an increase in HLA (MHC) class II (FIG. 7B), CD86 (FIG. 7C), and CD80 (FIG. 7D) on DC isolated from fragments after 7 days after treatment with anti-4-1BB.

Figure 7E:
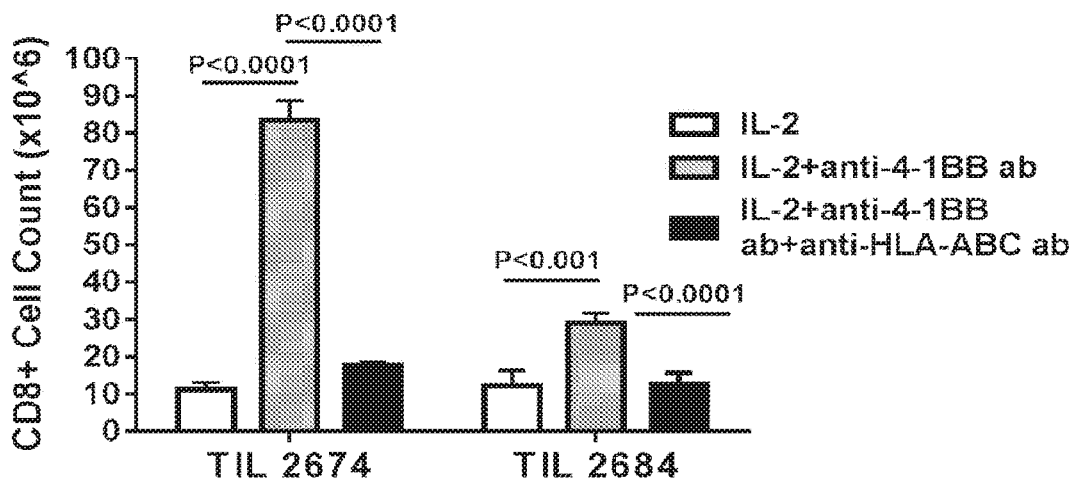

The observed persistence and activation of tumor fragment-resident DC with anti-4-1BB suggested that perhaps an ongoing presentation of antigen occurs in early tumor fragment cultures that may help drive CD8$^+$ TIL expansion. To test this, purified blocking anti-HLA-ABC antibody (W6/32) was added to the tumor fragment cultures on day 0, and the TIL that had grown out of the fragments harvested after 3 weeks. As shown in FIG. 7E, addition of anti-HLA-ABC antibody reversed the effect of the added anti-4-1BB on increasing the outgrowth of CD8$^+$ T cells, as measured by the decreased CD8$^+$ T-cell numbers.

Discussion

Adoptive cell therapy (ACT) with autologous TIL has shown considerable efficacy in mediating tumor regression and increasing the survival of metastatic melanoma patients that have failed first and second line therapies [Dudley, M E (2011) J Cancer 2:360-2; Rosenberg, S A, et al (2008) Nat Rev Cancer 8(4):299-308; Radvanyi, L G, et al (2012) Clin Cancer Res 18(24):6758-70]. Current response rates using a non-myeloablative chemotherapy pre-conditioning regimen of close to 40-50% have been observed at multiple centers now performing this therapy [Rosenberg, S A, et al (2008) Nat Rev Cancer 8(4):299-308; Radvanyi, L G, et al (2012) Clin Cancer Res 18(24):6758-70; Besser, M J, et al (2010) Clin Cancer Res 16(9):2646-55; Hershkovitz, L, et al (2010) Clin Dev Immunol 2010:260267]. With an increasing number of oncology centers world-wide performing TIL therapy, there is a growing interest in improving therapeutic efficacy and in making the TIL expansion process faster and more practical. CD8$^+$ T cells have emerged to be a key subset in mediating clinical response, although CD4$^+$ T cells in TIL products can also play sometimes a dominant role in tumor regression in less frequent cases [Friedman, K M, et al (2012) J Immunother 35(5):400-8]. A number of biological issues arise in making the TIL initial expansion process not only faster to reduce the wait times for patients, but also to enrich for tumor-reactive T cells, especially CD8$^+$ that also maintain effector-memory phenotypic properties for persistence after infusion.

However, although the culture of small 4-6 mm$^2$ tumor fragments cut from resected metastatic lesions has been used as the most common approach for initial melanoma TIL expansion with a long clinical history, there has been no attention paid to whether a viable tumor microenvironment persists in these fragments for a time and whether the microenvironment within these early fragment cultures can be modulated to affect the outcome of TIL expansion. Little is known about the dynamics of the early TIL expansion from tumor fragments and what processes take place within these small tumor pieces that can affect the yield and phenotype of the TILs that ultimately will control the nature of the infused cells and the clinical response. IL-2 has been used for years to expand TIL from these tumor fragments, but other non-cytokine immunomodulators that may play a role have not been investigated. Given the emerging importance of tumor-reactive CD8$^+$ TIL in ACT and the identification of early-intermediate T-cell activation markers on these cells marking tumor-specific TIL subsets, the above experiments were conducted to determine whether modulation of T-cell co-stimulatory pathways on these activated TIL, such as 4-1BB, could have profound effects on the yield of TIL and their phenotypic and functional properties that may be beneficial for ACT approaches. The above studies investigated whether provision of 4-1BB co-stimulation using agonist anti-4-1BB antibody right at the beginning of TIL expansion (to the tumor fragments) can modulate the tumor microenvironment within these early tumor fragment cultures and effect the yield of CD8$^+$ tumor-reactive as well as accelerate the rate of TIL outgrowth. The anti-4-1BB antibody was shown not only increases the rate of TIL expansion from tumor fragments, but also significantly increases the rate yield of CD8$^+$ T cells from the tumors while markedly enriching for tumor-specific CD8$^+$ TIL. Moreover, these properties were also maintained after further secondary rapid expansion (REP) with anti-CD3, irradiated PBMC feeder cells and IL-2 commonly used to generate the final TIL infusion products in clinical trials. In addition, although some markers like CD27 showed some down-modulation, overall treatment with anti-4-1BB did not seem to induce an over-differentiation of the CD8$^+$ TIL emanating from the tumor fragments and rather increased the expression of memory markers, such as bcl-2, bcl-6, and Eomes, while increasing the expression cytolytic granule markers such as Granzyme B.

The increased tumor reactivity observed in the TIL isolated from tumor fragment cultures treated with anti-4-1BB suggests that this may be an alternative approach at enriching TIL products for tumor specificity in adoptive transfer clinical trials to the direct isolation and purification of 4-1BB$^+$CD8$^+$ T cells from single cells digests of melanoma tumors.

The above data showing that blockade of HLA class I during early tumor fragment cultures can inhibit the increased outgrowth of CD8$^+$ T cells with anti-4-1BB also suggests that ongoing antigen presentation may actually occur in these tumor fragments that stimulate resident CD8$^+$ T cells which up-regulate 4-1BB and then get co-stimulated with the agonist antibody. This was also supported by the detection of NFκB activation and increased Ki67 expression in CD8$^+$ TTL isolated from both the tumor fragments and from the surrounding culture environment after 7 days when 4-1BB co-stimulation was provided. Thus, the antibody provides a potent signal enhancing CD8$^+$ co-stimulation leading to increased cell division in these early cultures.

To further dissect the effects of anti-4-1BB in the early tumor fragment cultures, its effects were examined on other leukocyte subsets in this system. Attention was focused on the tumor fragment-resident DC, as these cells are critical antigen-presenting cells in the tumor microenvironment activating resident CD8$^+$ T cells. A considerable sub-population of DC were found to express 4-1BB and addition of the agonist anti-4-1BB increased the expression of DC maturation markers such as MHC class II, CD86, and CD80. The increased expression of these DC maturation markers was also associated with the induction of NFκB activation in the DC induced by 4-1BB co-stimulation. Data from in vivo tumor model systems has also shown that DC are critical in driving localized T-cell activation and division in the tumor microenvironment [Benencia, F, et al (2011) J Biomed Biotechnol 2012:425476; Engelhardt, J J, et al (2012) Cancer Cell 21(3):402-17; Ma, Y, et al (2013) J Cancer 4(1):

36-44]. Thus, the tumor fragment culture system is an extension of this process which can be further enhanced by addition of immunomodulators such as 4-1BB agonists to improve the output and phenotype of TIL for adoptive cell therapy. Although 4-1BB expression was detected on the tumor fragment-resident DC, it could be that the agonist anti-4-1BB antibody indirectly induced DC maturation in the system or that such an indirect mechanism may have participated along with the direct activation of 4-1BB signaling in the DC. A marked increase in TNF-alpha, IFN-gamma and IL-6 produced during the first 7 days of tumor fragment culture was found when anti-4-1BB is added. TNF-alpha and IFN-gamma can also activate DC and thus these cytokines may be involved.

In summary, the tumor microenvironment was manipulated within early tumor fragment cultures from melanoma patients used to expand TIL for adoptive cell therapy. This can profoundly affect the outgrowth of tumor-reactive TIL associated with the modulation of tumor fragment-resident DC. This approach can be easily applied clinically to more rapidly expand TIL enriched for tumor specificity due to the availability of clinical-grade human or humanized anti-4-1BB antibodies such as the one used here. Moreover, the disclosed approach can be applied to improve the output of TILs from other solid tumors other than melanoma that have proven more difficult to expand tumor-reactive $CD8^+$ T cells maintaining effector and memory properties.

Example 2: TIL Therapy in Triple Negative Breast Cancer (TNBC)

Figure 11:
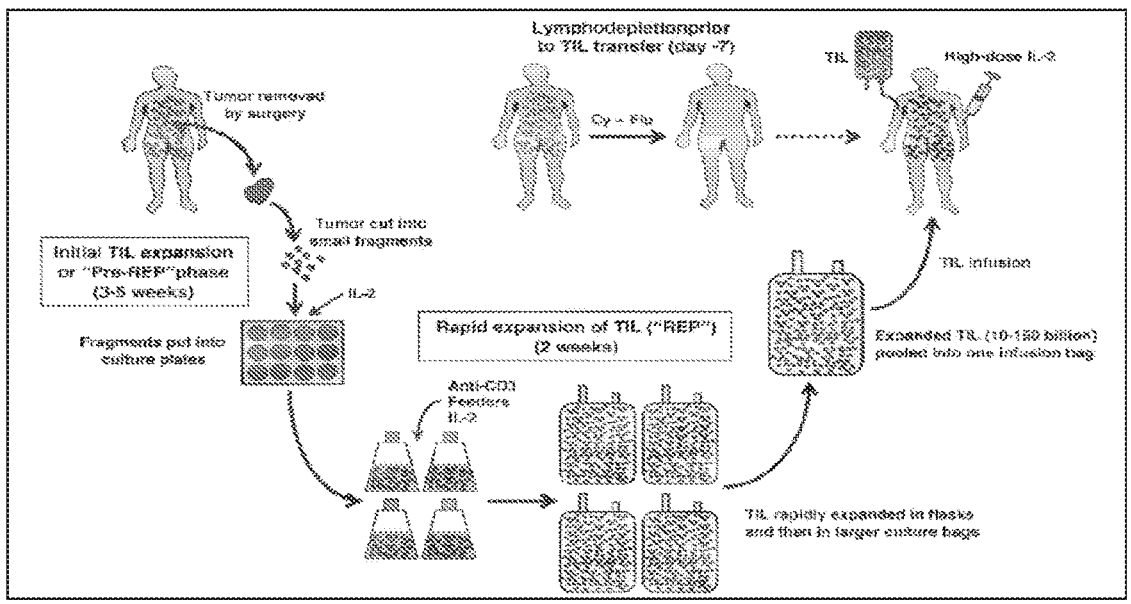
FIG. 11 is an illustration of the current adoptive T-cell therapy protocol for melanoma.

Triple negative breast cancer (TNBC) is the most aggressive form of breast cancer with few treatment options. Recently, it was shown that infiltration of TNBC with CD8+ tumor-infiltrating lymphocytes (TIL) is associated with improved prognosis, suggesting that T-cell responses at the tumor site can be harnessed as an autologous T-cell therapy for TNBC. Although TIL therapy has been developed for solid tumors such as melanoma (FIG. 11), cervical, and ovarian cancer, whether TIL, especially $CD8^+$ cells, with effector-memory properties can be expanded with reasonable yields from primary TNBC is not known. Given the high rates of relapse and refractory nature of recurrent TNBC disease, autologous TIL therapy may offer a life-saving option for these patients. Moreover, methods to facilitate $CD8^+$ TIL expansion from TNBC are also desirable given the cytotoxic potential of these cells. One approach to address this need is to manipulate TNF-R family member signaling, such as 41BB/CD137, to provide potent costimulatory signals for $CD8^+$ T-cell activation and division.

Patients and Methods

Figure 12:
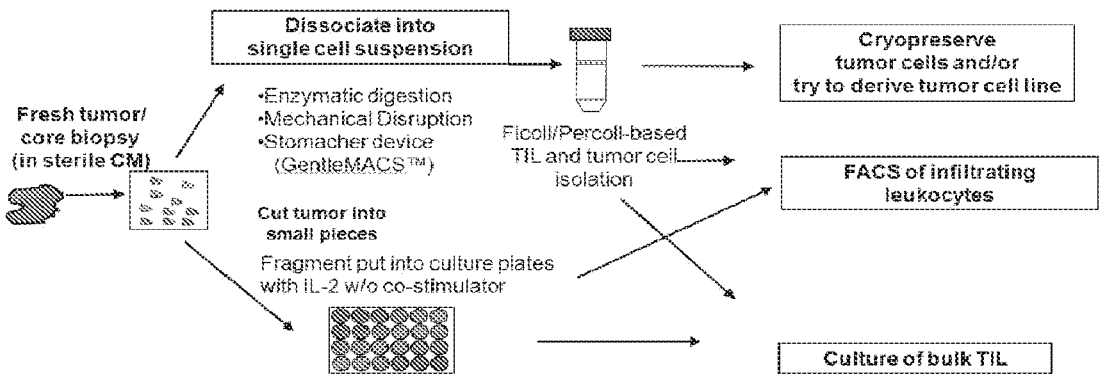
FIG. 12 is an illustration of a protocol used for tumor processing of Triple Negative Breast Cancers (TNBCs)/ Inflammatory Breast Cancers (IBC).
Figure 13A:
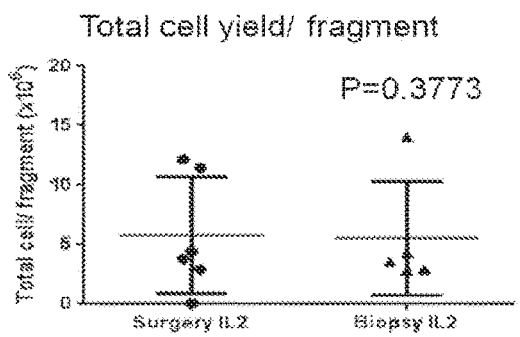
FIGS. 13A to 13D are plots showing the yield of total cell, CD8+ T cell, CD4+ T cell/fragment of lymphocytes from breast cancer.
Figure 13B:
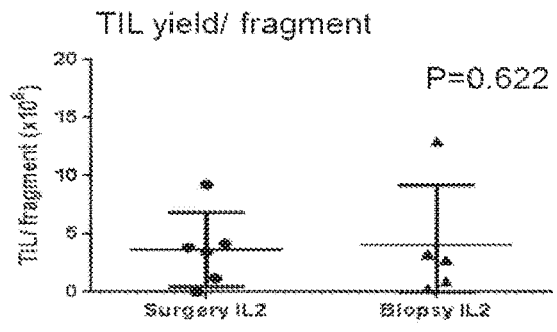
Figure 13C:
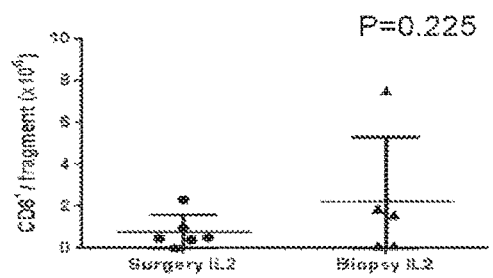
Figure 13D:
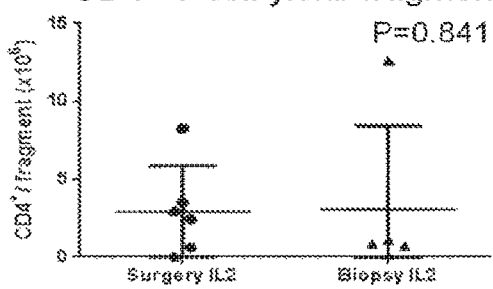

As illustrated in FIG. 12 and Table 1, four primary human TNBC tumor samples were obtained by surgical resection or core biopsy after neoadjuvant chemotherapy. Small tumor fragments were cultured in 24-well plates in medium containing 3000 IU/ml IL-2, or 3000 IU/ml IL-2 plus 10 µg/ml added agonistic anti-41BB IgG4 (BMS663513). Viable cell numbers and the expression of CD3, CD8, CD4, CD27, CD28, CCR7, CD45RA, CD56, CD16, Granzyme B, and Perforin was determined by flow cytometry on days 7, 14, 21, 28, and 35 after culture set-up. Cytotoxic function of the TIL was evaluated by measuring Caspase 3 cleavage in target cells.

TABLE 1

Tumor Processing for TNBC/IBC Protocol

| Case | Prior treatments | Age | Subtype | cStage | pStage | Grade | Method |
|---|---|---|---|---|---|---|---|
| 1 | Panitsumab, Abraxian, Carboplatin, FAC | 52 | IBC-TNBC | cT4dN3bM0 IIIc | ypT4bN3b | 2 | Enzymatic digestion |
| 2 | PTX, FAC | 63 | IBC-TNBC | cT4dNxM1 IV | ypT1miN2a | 3 | Enzymatic digestion Mechanical disruption |
| 3 | Capecitabine | 76 | IBC-TNBC | cT4dN2M0 IIIB | ypT4dN3 | 2 | Fragment |
| 4 | none | 71 | TNBC | cT1cN0M0 I | ypT1aN0 | 2 | Fragment |
| 5 | Ablaxane, FAC | 55 | TNBC | cT2N0M0 IIA | ypT1aN0 | 3 | Fragment |
| 6 | PTX, FAC | 57 | IBC-TNBC | cT4dN2M0 IIIB | ypT0N0 | 3 | Fragment |
| 7 | PTX, FAC | 34 | TNBC | cT2N1M0 IIB | ypT1cN1 | 3 | Fragment |
| 8 | PTX, FAC | 51 | TNBC | cT2N0M0 IIA | ypT1cN0 | 3 | Fragment |
| 9 | PTX, FAC | 79 | TNBC | cT3N1M0 IIIA | ypT2N0 | 3 | Fragment |

Figure 14A:
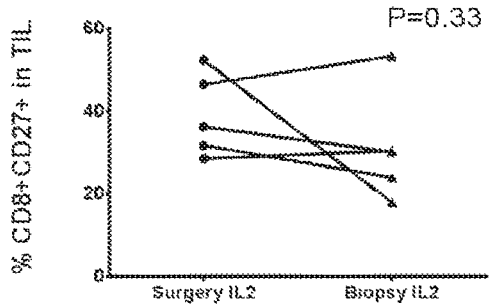
FIGS. 14A to 14B are plots showing that T cell differentiation was not different in TIL growth from surgical samples or biopsy samples.
Figure 14B:
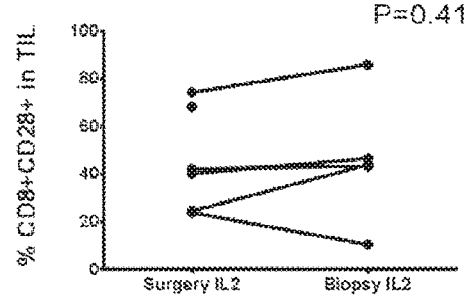
Figure 15A:
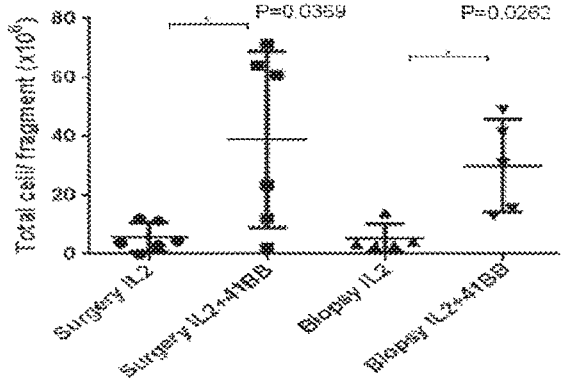
FIGS. 15A to 15C are plots showing addition of anti 4-1BB antibody increases total yield of isolated from breast cancer fragment after 4 weeks of culture with IL-2.
Figure 15B:
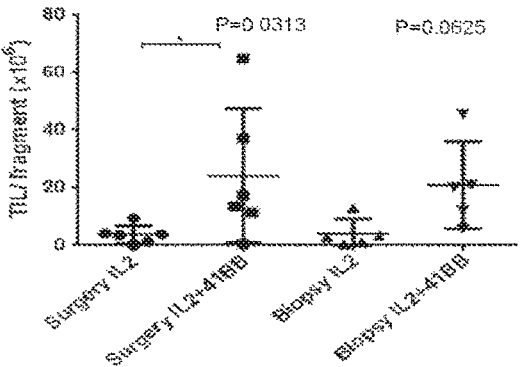
Figure 15C:
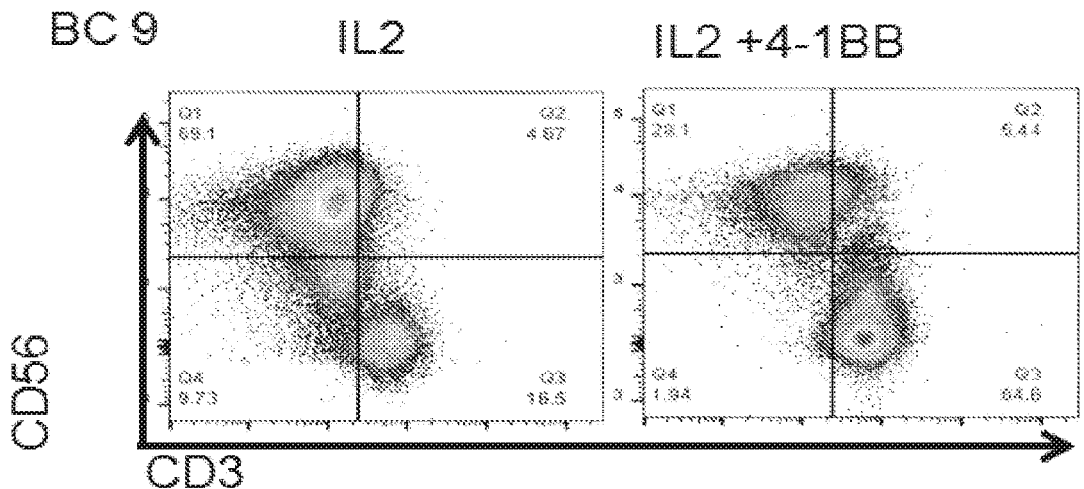
Figures 16A, 16B, 16C:
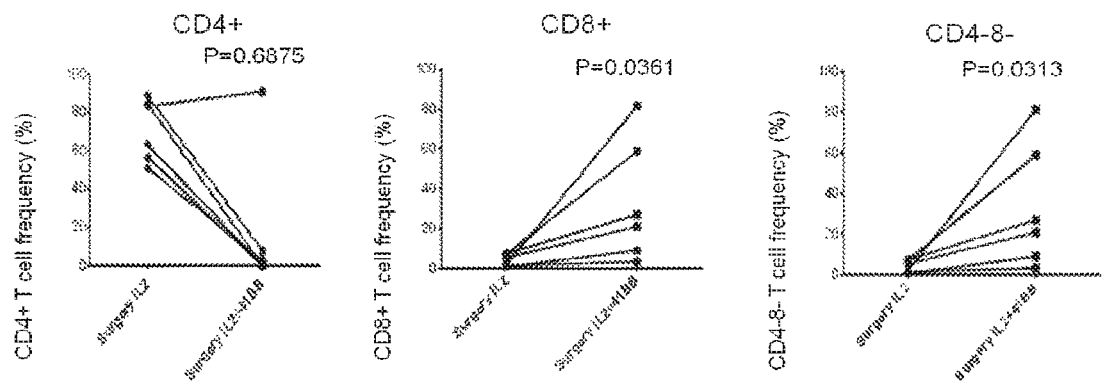
FIGS. 16A to 16E show that addition of anti 4-1BB antibody increases the frequency of CD8+ T cells and a CD4–CD8– T cell population expanded from tumor fragments.
Figure 16D:
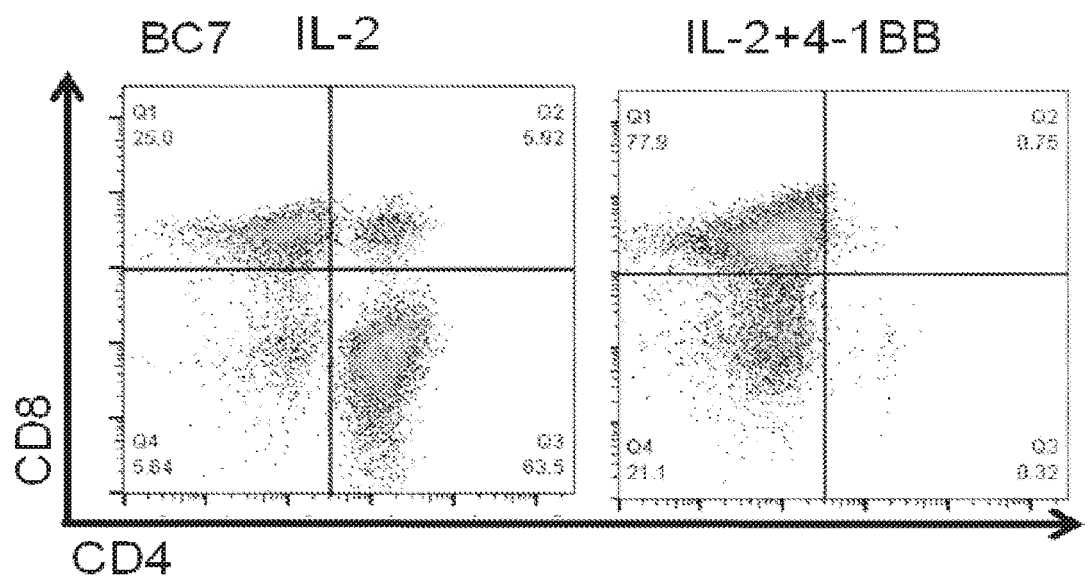
Figure 16E:
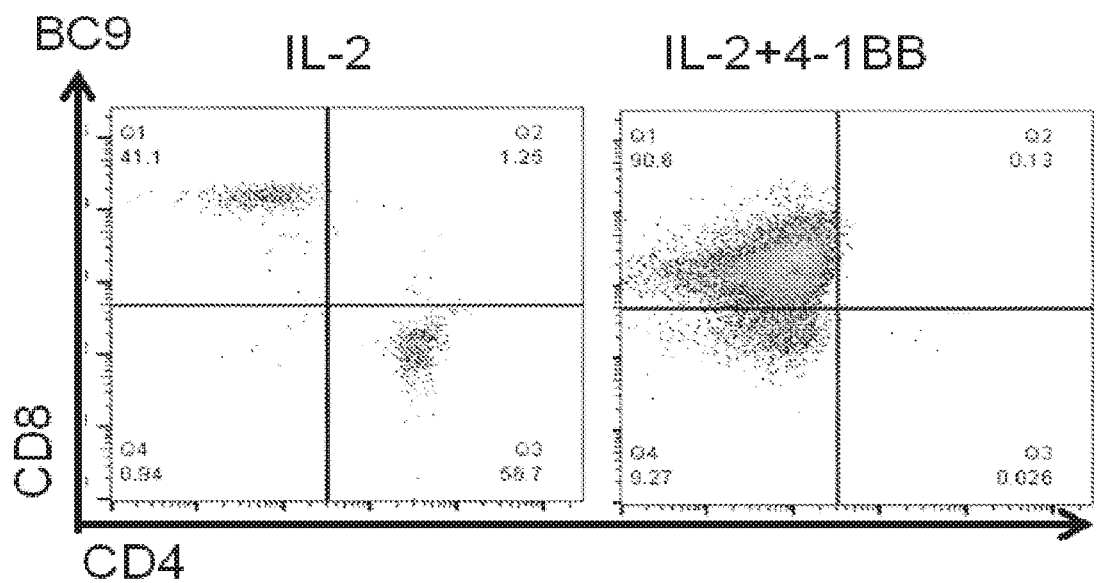
Figure 17A:
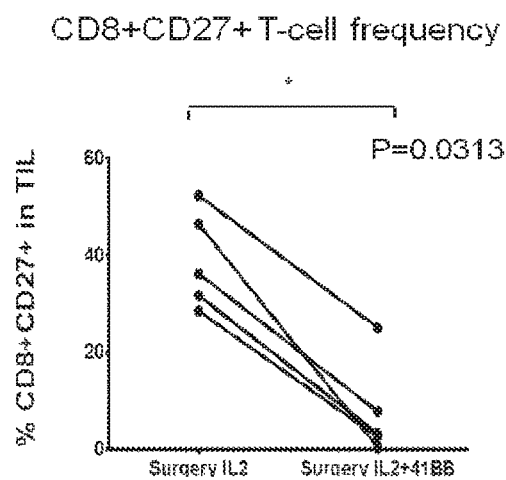
FIGS. 17A to 17C show that addition of anti-4-1BB to tumor fragments facilitates the expansion of more differentiated CD8+ TIL after 4 weeks of culture with IL-2.
Figure 17B:
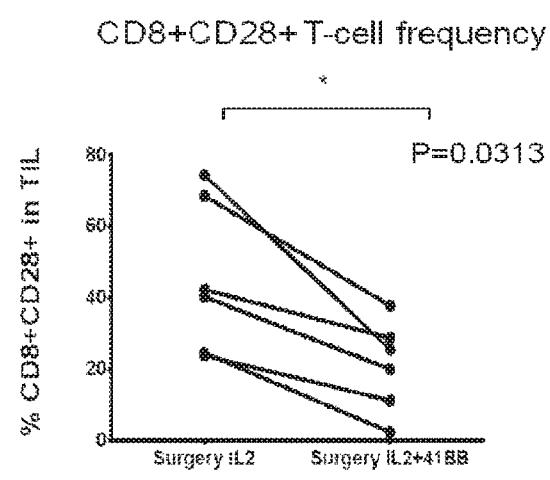
Figure 17C:
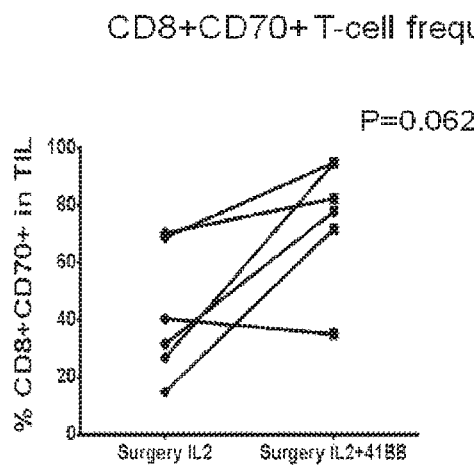
Figure 18A:
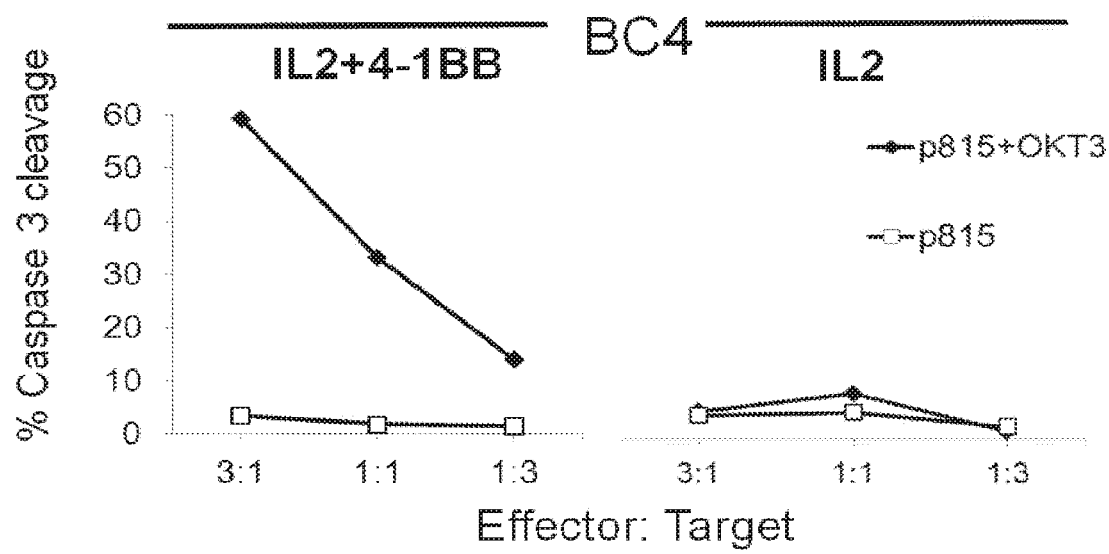
FIGS. 18A to 18D show that addition of anti 4-1BB to tumor fragments increases killing ability of expanded TIL after 4 weeks of culture with IL-2.
Figure 18B:
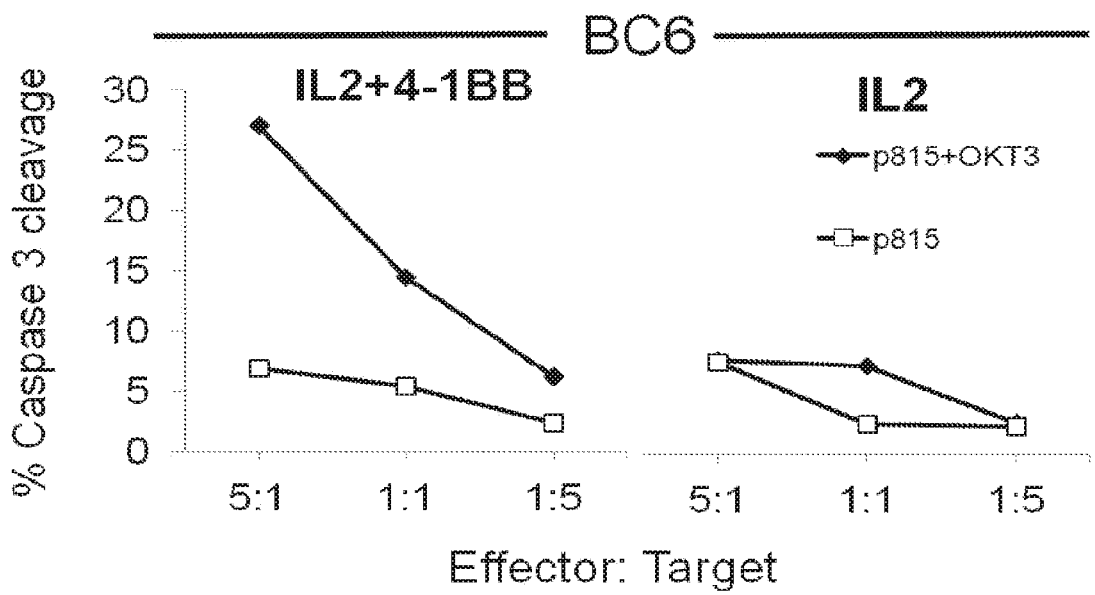
Figure 18C:
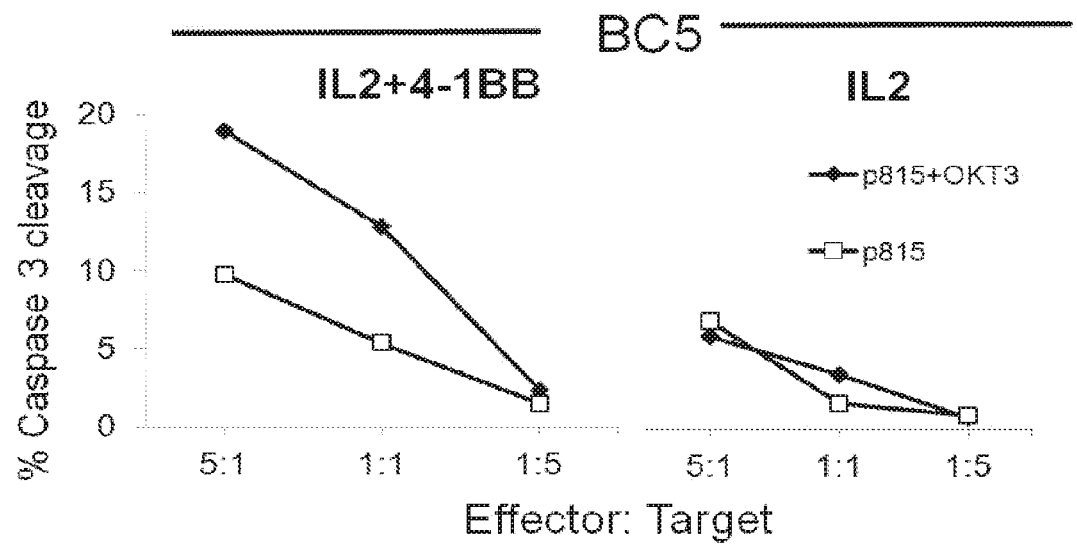
Figure 18D:
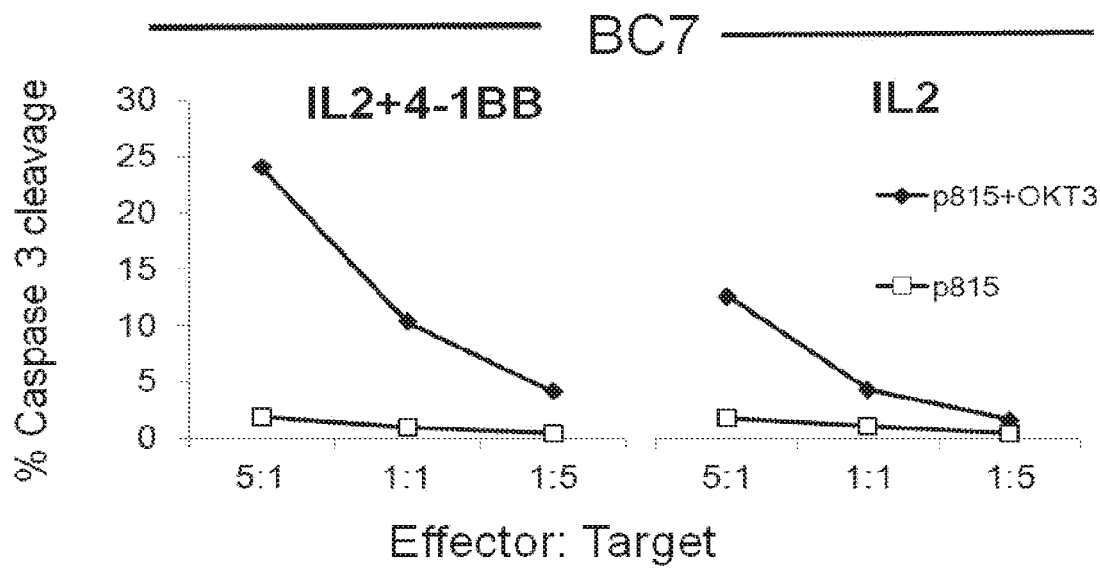

FAC: Anthracycline, 5FU, Cyclophosphamyde,
PTX: Paclitaxed,
Abraxian: Nab-Paclitaxel Results As shown in FIGS. 13A to 13D, the yield of total cells, $CD8^+$ T cell and $CD4^+$ T cell/fragment of lymphocytes from breast cancer tissue were not different in surgical and biopsy specimen. TILs were expanded with IL-2 (3,000 IU/ml) alone for 4 weeks. T cell differentiation was not different in TIL growth from surgical samples or biopsy samples (FIGS. 14A, 14B). As shown in FIGS. 15A to 15B, 4-1BB ligation increases the TIL expansion from both surgical and biopsy specimen. TILs were expanded with IL-2 from tumor fragments with or without a single addition of anti-4-1BB on day 0. Addition of anti 4-1BB antibody increases the frequency of CD8$^+$ T cells and a CD4$^-$CD8$^-$ T cell population expanded from tumor fragments (FIG. 16A-16E). 4-1BB ligation decreases the percentage of CD8$^+$CD27$^+$ T cell and CD8$^+$CD28$^+$ T cell population, which means 4-1BB antibody make T cell more differentiated (FIGS. 17A-17C).

TILs after 4 weeks of expansion were assayed for activity using flow-cytometry-based assay that measures caspase-3 cleavage using Fc receptor+P815 mastocytoma cells coated with anti-CD3 antibody in a redirected CTL assay (FIGS. 18A-18D). TILs expanded from TNBC tumor fragments treated with anti-4-1BB had increased the cleavage of CTL activity. No significant difference in Perforin or Granzyme B expression was found suggesting other mechanisms (e.g., enhanced degranulation ability), or increased expression of other cytolytic molecules, account for the increased CTL activity in TIL expanded with anti-4-1BB (FIGS. 19A-19B).

Although TILs were successfully expanded from the tumor fragments in 4/4 tumor samples, IL-2 alone yielded fewer cells than IL-2 together with 41BB costimulation provided early during the culture. Anti-41BB markedly increased the percentage and yield of CD8$^+$CD3$^+$ T cells at all times (6.34×10$^6$ vs 202×10$^6$). However, the resulting CD8$^+$ cells had decreased CD27 expression coincident with increased CD70 when anti-41BB was added. 41BB costimulation also increased the cytotoxic T-cell activity of the expanded TIL. The expanded TIL could also be cryopreserved and later expanded using anti-CD3 and IL-2.

Discussion

Disclosed is a method to expand CD8$^+$ TIL with cytotoxic activity with high yield from small samples of remaining primary tumor after neoadjuvant chemotherapy using TL-2. Provision of 41BB costimulation immediately upon tumor fragment culture initiation enhanced the rate and yield of CD8$^+$ T cells with increased effector function; these could be cryopreserved and later thawed with high viability for secondary expansion. The disclosed results support further development of an autologous TIL expansion protocol after neoadjuvant therapy for use in an adoptive cell therapy approach to treat TNBC recurrence or metastasis.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for ex vivo expansion of tumor-infiltrating lymphocytes (TILs), the method comprising:
   (a) culturing tumor fragments from a human subject in a first cell culture medium comprising IL-2 and a 4-1BB agonist antibody;
   (b) removing at least a plurality of the TILs; and
   (c) expanding the TILs in a second cell culture medium comprising IL-2, CD3 antibody, and irradiated peripheral blood mononuclear feeder cells.

2. The method of claim 1, wherein the 4-1 BB agonist antibody is present in the first medium at a concentration in the range of 0.5 g/mL to 10 g/mL.

3. The method of claim 1, wherein the 4-1BB agonist antibody is further added to the second culture medium at least every three days during step (c).

4. The method of claim 1, wherein the second culture medium further comprises a checkpoint inhibitor selected from the group consisting of an anti-PD-1 antibody, an anti-PD-L1 antibody, an anti-CTLA4 antibody, and a combination thereof.

5. The method of claim 1 further comprising selecting a subpopulation of the ex vivo expanded TILs that are CD8$^+$ and PD-1$^+$ from the total population of ex vivo expanded TILs.

6. A method for treating a tumor in a subject, comprising the steps of: (a) expanding tumor-infiltrating lymphocytes from a tumor fragment from the subject using the method of claim 1; (b) treating the subject with nonmyleoablative lymphodepleting chemotherapy; and (c) administering the tumor-infiltrating lymphocytes to the subject.

7. The method of claim 1, wherein the IL2 is present in the first medium at a concentration of 3000 IU/ml or 6000 IU/mL.

8. The method of claim 1, wherein the IL2 is present in the second medium at a concentration of 3000 IU/ml or 6000 IU/mL.

9. The method of claim 1, further comprising, prior to the culturing, enzymatically digesting the tumor fragments using a digest mixture.

10. The method of claim 9, wherein the digest mixture comprises a deoxyribonuclease (DNase), a collagenase, a hyaluronidase, or a combination thereof.

11. The method of claim 1, wherein the CD3 antibody is present at an initial concentration of 30 ng/mL in the second cell culture medium.

12. The method of claim 1, wherein the expanded TILs comprise T cells with a phenotype selected from the group consisting of CD3$^+$CD4$^+$, CD3$^+$CD8$^+$, CD8$^+$CD28$^+$, CD8$^+$CD27$^+$, CD8$^+$CD27$^+$CD28$^+$, and combinations thereof.

13. The method of claim 1, wherein the irradiated peripheral blood mononuclear feeder cells comprise irradiated autologous lymphocytes.

14. The method of claim 1, wherein the irradiated peripheral blood mononuclear feeder cells comprise irradiated allogenic lymphocytes.

15. The method of claim 14, wherein the irradiated allogenic lymphocytes are human leukocyte antigen A2 (HLA-A2) positive.

* * * * *